(12) United States Patent
Iwamiya

(10) Patent No.: US 11,096,969 B2
(45) Date of Patent: Aug. 24, 2021

(54) COMPOSITION FOR INJECTION WHICH CAN BE USED FOR TREATMENT OF HEART DISEASES AND CONTAINS FIBROBLASTS, AND METHOD FOR PRODUCING FIBROBLAST FOR THERAPY USE

(71) Applicant: METCELA INC., Yamagata (JP)

(72) Inventor: Takahiro Iwamiya, Yamagata (JP)

(73) Assignee: Metcela, Inc., Yamagata (JP)

( * ) Notice: Subject to any disclaimer, the term of this patent is extended or adjusted under 35 U.S.C. 154(b) by 0 days.

(21) Appl. No.: 16/263,321

(22) Filed: Jan. 31, 2019

(65) Prior Publication Data

US 2019/0224250 A1   Jul. 25, 2019

Related U.S. Application Data

(63) Continuation-in-part of application No. PCT/JP2018/006795, filed on Feb. 23, 2018.

(30) Foreign Application Priority Data

Feb. 24, 2017 (JP) .............................. JP2017-033624

(51) Int. Cl.
  *A61K 35/33*   (2015.01)
  *A61P 9/04*   (2006.01)
  *A61P 9/10*   (2006.01)
  *A61K 9/00*   (2006.01)

(52) U.S. Cl.
  CPC ............ *A61K 35/33* (2013.01); *A61K 9/0019* (2013.01); *A61P 9/04* (2018.01); *A61P 9/10* (2018.01)

(58) Field of Classification Search
  None
  See application file for complete search history.

(56) References Cited

U.S. PATENT DOCUMENTS

| | | | | |
|---|---|---|---|---|
| 2004/0002740 A1* | 1/2004 | Lee | ...................... | A61B 17/3478 607/9 |
| 2004/0005295 A1* | 1/2004 | Lee | ........................ | A61K 35/36 424/93.2 |
| 2004/0161412 A1* | 8/2004 | Penn | ....................... | A61K 35/28 424/93.7 |
| 2006/0057124 A1 | 3/2006 | Shim et al. | | |
| 2007/0219487 A1* | 9/2007 | Mazgalev | ............... | A61K 35/34 604/93.01 |
| 2015/0297794 A1 | 10/2015 | Yamashita et al. | | |
| 2017/0112880 A1 | 4/2017 | Iwamiya et al. | | |

FOREIGN PATENT DOCUMENTS

| | | |
|---|---|---|
| JP | 2010 81829 A | 4/2010 |
| JP | 2016 027797 A | 2/2016 |
| JP | 2016 519938 A | 7/2016 |
| WO | WO-2013/028968 A1 | 2/2013 |
| WO | WO-2013/137491 A1 | 9/2013 |
| WO | WO-2014039995 A1 * | 3/2014 |
| WO | WO-2014/188170 A1 | 11/2014 |
| WO | WO 2016/006262 A1 | 1/2016 |

OTHER PUBLICATIONS

Chang et al., (Cell Physiol. Biochem., 34:703-714 (2014).*
Louault et al., Biochimica et Biophysica Acta, 1778:2097-2104 (2008).*
Matsuura et al., Biomater., 32:7355-7362 (2011).*
Zhang et al (Cell Commun. Adhes. 15(3):289-303 (2008).*
Iwamiya et al., Regen. Ther., 4:92-102 (2016).*
Furtado et al., Develop., 143:387-397 (2016) (Year: 2016).*
Ieda et al., Cell, 142:375-386 (2010) (Year: 2010).*
Thai et al., Cell Transplant., 18:283-295 (2009) (Year: 2009).*
Blasi et al., Vasc. Cell, 3(5):1-14 (2011) (Year: 2011).*
Zhang et al., Mol. Carcinogen., 12:50-58 (1995) (Year: 1995).*
Faniku et al., Int. J. Mol. Sci. 19(604):1-16 (2018) (Year: 2018).*
Ruiz-Villalba et al., PLoS ONE 8(1):e53694 (2013) (Year: 2013).*
International Search Report and Written Opinion for corresponding International Application No. PCT/JP2018/006795, dated Apr. 10, 2018.
Li et al., Connexin 43 gene-modified BMSCs for treating myocardial infarction, South China Journal of Cardiology, 2011, vol. 12, pp. 112-117.
Takahiro Iwamiya., "Discovery of a specific type of cardiac fibroblasts ameliorating chronic heart failure",Baiosaiensu To Indasutori—Bioscience to Industry, Japan Bioindustry Association, JP, vol. 76, dated Jan. 1, 2018.
Katsuhisa Matsuura et al: Transplantation of cardiac progenitor cells ameliorates cardiac dysfunction after myocardial infarction in mice, Journal of Clinical Investigation, dated Jul. 13, 2009.
"Methocera confirms therapeutic effect in rats Cell therapy for heart failure: Nikkei", dated Sep. 18, 2017.
Extended European Search Report for European Patent Application No. 18758465.1 dated Jan. 24, 2020.

* cited by examiner

*Primary Examiner* — Thomas J. Visone
(74) *Attorney, Agent, or Firm* — Alston & Bird LLP

(57) ABSTRACT

The present invention aims to provide a method which has not been established yet and which is useful for achieving long-term and fundamental cure of a necrotic cardiac tissue region to allow recovery of functionality of the heart.
The present invention provides an injectable composition for treatment of a cardiac disease, the composition comprising fibroblasts, wherein the fibroblasts contain CD106-positive fibroblasts, preferably contain CD90-positive fibroblasts, and the fibroblasts do not form colonies.

5 Claims, 23 Drawing Sheets

VCF : CD106-positive rat cardiac fibroblast (A)

(B)

(C)

(D)

VCF : CD106-positive human cardiac fibroblast (A)

(B)

(C)

(D)

VCFs(x20) VCFs(x200)

MSCs(x20) MSCs(x200)

COMPOSITION FOR INJECTION WHICH CAN BE USED FOR TREATMENT OF HEART DISEASES AND CONTAINS FIBROBLASTS, AND METHOD FOR PRODUCING FIBROBLAST FOR THERAPY USE

CROSS-REFERENCE TO RELATED APPLICATION

This is a continuation-in-part of International Application PCT/JP2018/006795, filed on Feb. 23, 2018, and designated the U. S., and claims priority from Japanese Patent Application 2017-033624 which was filed on Feb. 24, 2017, the entire contents of which are incorporated herein by reference.

TECHNICAL FIELD

The present invention relates to an injectable composition for treatment of a cardiac disease, the composition comprising fibroblasts, more specifically, relates to an injectable composition for treatment of a cardiac disease, the composition comprising fibroblasts expressing a particular protein. The present invention also relates to a method for producing fibroblasts for treatment, which fibroblasts can be used for an injectable composition.

BACKGROUND

The survival prognosis after heart failure due to myocardial infarction or cardiomyopathy is very poor, and its fundamental therapeutic method, at present, is limited to heart transplantation. However, at present, patients are suffering from insufficiency of the number of donors worldwide rather than only in Japan, and cannot receive sufficient therapy, which is problematic. Therefore, in recent years, treatment of cardiac diseases by regenerative medicine is drawing attention, and its technologies are being developed.

For example, JP 2010-081829 A and the like disclose cell sheets, and development of such sheets to autologous skeletal myoblasts is being studied. WO 2013/137491 and the like study treatment of a cardiac disease with a myocardial sheet that uses induced pluripotent stem cells.

However, in spite of these studies, there has been no report on a method that enables long-term and significant recovery of a cardiac function that has been lost, and there is a demand for establishment of a method that enables long-term and fundamental cure of a necrotic cardiac tissue region to allow recovery of a heart function.

Under such circumstances, the present inventors discovered that a functional cardiac cell sheet can be obtained using fibroblasts that are positive for vascular cell adhesion molecule-1 (VCAM-1, CD106) (see WO 2016/006262).

SUMMARY

An object of the present invention is to provide a method which has not been established yet and which is useful for achieving long-term and fundamental cure of a necrotic cardiac tissue region to allow recovery of a heart function.

The present inventors carried out a study in order to solve the above problem, and, as a result, discovered that a heart disease can be treated by administration (infusion) of a particular kind of fibroblasts to a necrotic cardiac tissue region. An embodiment of the present invention may include the following first aspect (Embodiment A).

(A1) An injectable composition for treatment of a cardiac disease, the composition comprising fibroblasts, wherein the fibroblasts contain fibroblasts that are positive for vascular cell adhesion molecule-1 (VCAM-1, CD106).
(A2) The injectable composition according to (A1), wherein the fibroblasts contain fibroblasts that are positive for Thymus cell antigen-1 (Thy-1, CD90).
(A3) The injectable composition according to (A1) or (A2), wherein the fibroblasts contain fibroblasts positive for connexin 43 (Cx43).
(A4) The injectable composition according to any one of (A1) to (A3), wherein the ratio (in terms of the cell number) of the CD106-positive fibroblasts to the total amount of fibroblasts contained in the injectable composition is not less than 0.03%.

The present invention may also include the following second aspect (Embodiment B).
(B1) A method for producing fibroblasts for treatment, the method comprising the steps of:
   providing fibroblasts; and
   screening CD106-positive fibroblasts from the fibroblasts.
(B2) The production method according to (B1), wherein the fibroblasts for treatment are used for treatment of a cardiac disease.
(B3) The production method according to (B1) or (B2), further comprising a step of screening of CD90-positive cells from fibroblasts.
(B4) The production method according to any one of (B1) to (B3), wherein the fibroblasts for treatment contain connexin 43-positive fibroblasts.
(B5) The production method according to any one of (B1) to (B4), wherein the ratio (in terms of the cell number) of the CD106-positive fibroblasts to the total cell amount of the fibroblasts for treatment is not less than 0.03%.

The present invention may also include the following third aspect (Embodiment C).
(C1) A method for treatment of a heart disease, comprising carrying out injection of an injectable composition containing fibroblasts into a necrotic cardiac tissue region or a vicinity thereof, and/or infusion of the composition into a coronary artery, wherein the fibroblasts contain CD106-positive fibroblasts.
(C2) The method for treatment of a heart disease according to (C1), wherein the fibroblasts contain CD90-positive fibroblasts.
(C3) The method for treatment of a heart disease according to (C1), wherein the fibroblasts contain connexin 43-positive fibroblasts.
(C4) The method for treatment of a heart disease according to (C1), wherein the ratio (in terms of the cell number) of the CD106-positive fibroblasts to the total amount of fibroblasts contained in the injectable composition is not less than 0.03%.

The present invention may also include the following fourth aspect (Embodiment D).
(D1) Use of fibroblasts as an injectable composition, wherein the fibroblasts contain CD106-positive fibroblasts.
(D2) The use according to (D1), wherein the fibroblasts contain CD90-positive fibroblasts.
(D3) The use according to (D1) or (D2), wherein the fibroblasts contain connexin 43-positive fibroblasts.
(D4) The use according to any one of (D1) to (D3), wherein the ratio (in terms of the cell number) of the CD106-positive fibroblasts to the total amount of fibroblasts contained in the injectable composition is not less than 0.03%.

By the embodiments of the present invention, means effective for curing a necrotic cardiac tissue region to recover a cardiac function is provided.

DETAILED DESCRIPTION

Figure 1A:
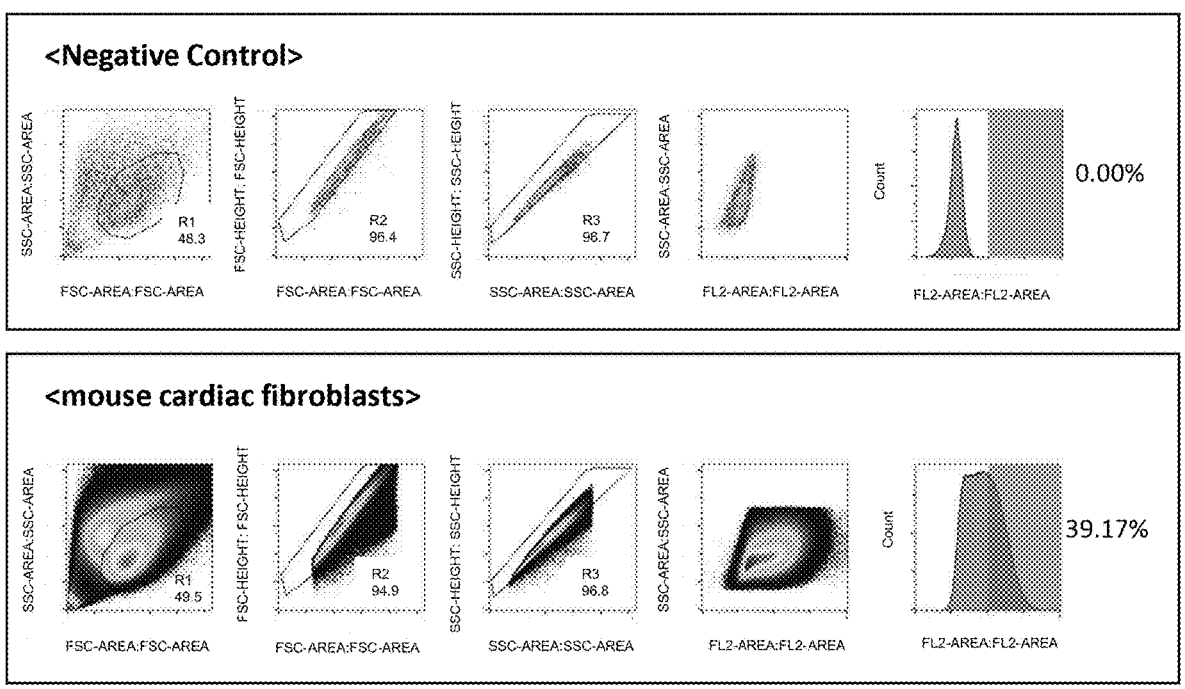
FIG. 1A shows graphs illustrating localization of VCAM-1 protein in CD106-positive mouse cardiac fibroblasts.

The present invention is described below in detail by way of specific embodiments. However, the present invention is not limited to the specific embodiments described.

One embodiment of the present invention is an injectable composition for treatment of a cardiac disease, the composition comprising fibroblasts, wherein the fibroblasts contain CD106-positive (hereinafter also referred to as CD106+) fibroblasts.

The fibroblasts include any cells that eventually become fibroblasts or myofibroblasts. That is, the scope of the fibroblasts in the present embodiment includes cells which are in the process of differentiation or maturation and which eventually become fibroblasts or myofibroblasts even in cases where the cells cannot be identified as the fibroblasts or the myofibroblasts at that time point. The scope of the fibroblasts in the present embodiment also includes cells that are not called fibroblasts, such as stromal cells, precursor cells, stem cells, and myoblasts, as long as they are CD106+ cells having functions similar to those of fibroblasts.

CD106+ fibroblasts are characterized in that they are positive for vimentin, which is a cytoskeletal marker of fibroblasts and mesenchymal stem cells, and negative for STRO-1, which is one of the best known molecular markers of mesenchymal stem cells (MSCs).

The origin of the fibroblasts is not limited, and these cells may be obtained by differentiation of pluripotent stem cells or multipotent stem cells such as embryonic stem cells (ES cells), induced pluripotent stem cells (iPS cells), or Muse cells, or of adult stem cells such as mesenchymal stem cells. Primary cells collected from an animal (including human) may be used, or an established cell line may be used. Heart-derived fibroblasts are preferably used, and epicardium-derived fibroblasts are more preferably used.

In particular, when fibroblasts derived from human are used, a high therapeutic effect on a heart disease can be obtained by injection. Fibroblasts derived from human, compared to mouse and the like, show a much lower ratio of CD106+ fibroblasts. According to a study by the present inventors, the ratio is at most about 9.1% (in terms of the cell number). Thus, the present invention may also include a human-derived fibroblast population in which the ratio of human-derived CD106+ fibroblasts is increased by the later-mentioned screening step and/or the like. For example, another aspect of the present invention may be a human-derived fibroblast population in which the ratio (in terms of the cell number) of human-derived CD106+ fibroblasts in total human-derived fibroblasts is not less than 10%. The ratio (in terms of the cell number) of CD106+ fibroblasts in total fibroblasts may be not less than 15%, may be not less than 20%, may be not less than 25%, may be not less than 30%, may be not less than 40%, may be not less than 50%, may be not less than 60%, may be not less than 70%, may be not less than 80%, may be not less than 90%, or may be 100%. The human-derived fibroblast population herein may be a human heart-derived fibroblast population, may be human adult heart-derived fibroblasts, or may be a human fetal heart-derived fibroblast population.

By selecting cells known to be CD106+, the process of cell sorting can be omitted.

CD106, also called VCAM-1, is a protein known as a cell adhesion molecule expressed in vascular endothelial cells and the like. In the present embodiment, CD106+, that is, VCAM-1-positive (VCAM-1+) fibroblasts are used as an injectable composition for treatment of a heart disease.

The CD106+ fibroblasts used as an injectable composition enable treatment of a heart disease by direct injection into a necrotic myocardial tissue region. Further, the cells may be injected into the vicinity of a necrotic myocardial tissue region, may be infused into a coronary artery, or may be infused into a vein, artery, lymph node, or lymph vessel. The infusion into a coronary artery, or the infusion into a vein, artery, or lymph vessel may be carried out either by injection into the vessel or by infusion through a catheter, or another known method may be used therefor.

The method of the injection is not limited, and a known injection method such as needle injection or needle-free injection may be applied thereto. The method of infusion using a catheter is also not limited, and a known method may be applied thereto.

The injectable composition may also contain another kind of fibroblasts or another component as long as the composition contains a therapeutically effective amount of CD106+ fibroblasts as an effective component. In cases where another kind of fibroblasts are contained, the ratio of the CD106+ fibroblasts to the total amount of fibroblasts contained in the injectable composition in terms of the cell number may be not less than 0.03%, may be not less than 0.1%, may be not less than 1%, may be not less than 2%, may be not less than 4%, may be not less than 5%, may be not less than 10%, may be not less than 20%, may be not less than 30%, may be not less than 40%, may be not less than 50%, may be not less than 60%, may be not less than 70%, may be not less than 80%, may be not less than 90%, may be not less than 95%, may be not less than 98%, or may be not less than 99%.

The CD106+ fibroblasts contained in the injectable composition may be cells prepared by co-culture with other cells, for example, cardiomyocytes.

The CD106+ fibroblasts contained in the injectable composition may not form colonies. Generally speaking, stem cells have a function of forming colonies, however, fibroblasts of the present embodiment do not form colonies. Cells having a function of forming colonies may cause a cancerization, clogs in the injection catheter, embolized vessel of the heart, or the like after injection of the cells into a necrotic myocardial tissue region.

Examples of the heart disease in the present embodiment include, but are not limited to, diseases caused by disorder, deficiency, dysfunction, or the like of a myocardial tissue, such as heart failure, ischemic heart diseases, myocardial infarction, cardiomyopathy, myocarditis, hypertrophic cardiomyopathy, and dilated cardiomyopathy.

The CD106+ fibroblasts contained in the injectable composition may be CD90-positive (CD90+). That is, the injectable composition may contain CD90-positive fibroblasts. CD90, also called Thy-1, is a glycosyl-phosphatidylinositol (GPI)-linked molecule rich in sugar chains. CD90 is expressed in various stromal cell lines of nerve tissues, connective tissues, and the like, but is not expressed in cardiomyocytes. Thus, the term "CD90+ fibroblasts" is meant to be free of cardiomyocytes. For the term "CD90+ fibroblasts free of cardiomyocytes" as used herein, the presence of some amount of cardiomyocytes is acceptable. The amount of cardiomyocytes may be not more than 5%, not more than 4%, not more than 3%, not more than 2%, not more than 1%, not more than 0.5%, not more than 0.1%, or not more than 0.01% in terms of the cell number with respect to the total cells contained in the injectable composition.

The ratio (in terms of the cell number) of CD90+ fibroblasts in the CD106+ fibroblasts may be not less than 30%, may be not less than 40%, may be not less than 50%, may be not less than 60%, may be not less than 70%, may be not less than 80%, may be not less than 90%, may be not less than 95%, may be not less than 98%, or may be 100%.

In certain embodiment of the present invention, a fibroblast population containing CD106+CD90+ fibroblasts may be provided. In the fibroblast population, the ratio of CD106+CD90+ fibroblasts in terms of the cell number may be more than 8.2%, not less than 8.5%, not less than 9%, not less than 10%, not less than 15%, not less than 20%, not less than 30%, not less than 40%, not less than 50%, not less than 60%, not less than 70%, not less than 80%, not less than 90%, not less than 95%, not less than 97%, not less than 98%, not less than 99%, or 100%. In these modes, the CD106+CD90+ fibroblasts may be, for example, derived from human. In these embodiments, the CD106+CD90+ fibroblasts may be, for example, heart-derived fibroblasts. In these embodiments, the CD106+CD90+ fibroblasts may be, for example, human heart-derived fibroblasts. The CD106+CD90+ fibroblasts can be obtained by, for example, concentrating CD106+CD90+ cells from a tissue using a cell sorter or the like. In these modes, the fibroblasts may be fibroblasts collected from a human fetus.

CD106+CD90+ fibroblasts are capable of controlling inflammatory response by secretion of cytokines and the like for maintenance of homeostasis of organs. The secreted cytokines, chemokines, and the like form microenvironments suitable for regeneration of cardiac muscle tissues, and promote the growth of cardiomyocytes, control of beating of cardiomyocytes, and/or angiogenesis, thereby allowing improvement of cardiac functions. Further, CD106+CD90+ fibroblasts are capable of suppressing the progression of fibrosis.

Accordingly, the present description may include an invention of a cardiac inflammatory response controlling agent (or a cardiac inflammation suppressing agent) containing CD106+CD90+ fibroblasts or a purified product of the cells. The present description may also include an invention of a cytokine secretion promoting agent for cardiac cells, which agent contains CD106+CD90+ fibroblasts or a culture supernatant of these cells; or a cytokines secretion controlling agent containing a cell lysate or a culture supernatant of CD106+CD90+ fibroblasts, or containing a purified product of these cells. The present description may also include an invention of a microenvironment forming agent for cardiac tissues, which agent contains CD106+CD90+ fibroblasts. The present description may also include an invention of a cardiomyocyte growing agent, a beat controlling agent for cardiomyocytes, or an agent for promoting maturation or angiogenesis of cardiomyocytes, containing CD106+CD90+ fibroblasts.

In other words, a method for controlling cardiac inflammatory response, which method includes a step of injecting CD106+CD90+ fibroblasts into a necrotic cardiac tissue region or the vicinity thereof, and/or infusing these cells into a coronary artery, may be provided. Further, a method for controlling secretion of cytokines or a method for promoting secretion of cytokines, which method includes a step of injecting CD106+CD90+ fibroblasts into a necrotic cardiac tissue region or the vicinity thereof, and/or infusing these cells into a coronary artery, may be provided. Further, a method for forming a microenvironment in a cardiac tissue, which method includes a step of injecting CD106+CD90+ fibroblasts into a necrotic cardiac tissue region or the vicinity thereof, and/or infusing these cells into a coronary artery, may be provided.

The cytokines are proteins responsible for signal transduction involved in immunity or inflammation, and include known cytokines.

The CD106+ fibroblasts contained in the injectable composition may be connexin 43-positive (connexin 43+) fibroblasts. That is, the injectable composition may contain connexin 43-positive fibroblasts.

Connexin 43 is a transmembrane protein which is known to be expressed in endothelial cells and smooth muscle cells in the vascular wall together with arteriosclerotic plaques, and to bind, as a gap junction of a cardiomyocyte, to an adjacent cell to be involved in propagation of electrical excitation of the heart. Present inventors think that the connexin 43 positivity enables transmission of electric signals in a myocardial tissue, leading to improvement of the therapeutic effect of the injectable composition.

The ratio (in terms of the cell number) of connexin 43+ fibroblasts in the CD106+ fibroblasts may be not less than 30%, may be not less than 40%, may be not less than 50%, may be not less than 60%, may be not less than 70%, may be not less than 80%, may be not less than 90%, may be not less than 95%, may be not less than 98%, or may be 100%.

The injectable composition may contain other components physiologically acceptable as an injectable composition. Examples of such other components include physiological saline, cell preservation liquids, cell culture media, hydrogels, extracellular matrices, and cryopreservation liquids.

The ratio of the CD106+ fibroblasts contained in the injectable composition may be appropriately set based on, for example, the mode of injection or infusion such that a therapeutically effective amount of the CD106+ fibroblasts are contained as an effective component. Usually, the ratio, in terms of the cell number, of CD106+ fibroblasts to the total amount of cells in the injectable composition may be not less than 0.03%, may be not less than 1%, may be not less than 5%, may be not less than 10%, may be not less than 25%, may be not less than 50%, may be not less than 90%, may be not less than 95%, may be not less than 98%, or may be 100%.

The number of CD106+ fibroblasts contained in the injectable composition may be, for example, not less than $1.0 \times 10^2$ cells/mL, not less than $1.0 \times 10^3$ cells/mL, not less than $1.0 \times 10^4$ cells/mL, not less than $1.0 \times 10^5$ cells/mL, not less than $5.0 \times 10^6$ cells/mL, or not less than $1.0 \times 10^7$ cells/mL. The number of CD106+CD90+ fibroblasts contained in the injectable composition may be, for example, not less than $1.0 \times 10^2$ cells/mL, not less than $1.0 \times 10^3$ cells/mL, not less than $1.0 \times 10^4$ cells/mL, not less than $1.0 \times 10^5$ cells/mL, not less than $5.0 \times 10^6$ cells/mL, or not less than $1.0 \times 10^7$ cells/mL. The number of CD106+ fibroblasts contained in the injectable composition may be further increased or decreased depending on conditions of the cardiac disease.

The method for producing the fibroblasts contained in the injectable composition is described below. For the method for producing the fibroblasts, one may refer to a previous report by the present inventors (WO 2016/006262, which is hereby incorporated by reference), and the method may be carried out according to this report.

(Step of Providing Fibroblasts)

In the step of providing the fibroblasts, the origin of the fibroblasts is not limited as mentioned above. An embodiment based on autologous transplantation may be employed, and, in such cases, cardiac fibroblasts isolated from a cardiac tissue of a patient with a cardiac disease, or cardiac fibroblasts isolated after differentiation of adult (somatic) stem cells of a patient, are provided. The fibroblasts may also be fibroblasts collected after differentiation of iPS cells. Further, an embodiment based on allogeneic transplantation may be employed, and, in such cases, cardiac fibroblasts isolated from a cardiac tissue derived from a donor who provides cardiac cells, or isolated from a cardiac tissue prepared using an animal or the like; or cardiac fibroblasts isolated after differentiation of adult (somatic) stem cells of a donor; are provided. The fibroblasts may also be fibroblasts collected after differentiation of iPS cells derived from a donor.

(Step of Separation of Fibroblasts)

The provided fibroblasts may typically be subjected to treatment using an enzyme such as dispase or collagenase, to achieve isolation for culture. The separation may be carried out either with the enzyme such as dispase or collagenase, or by another treatment such as a mechanical treatment as long as it allows the separation required before the primary culture.

(Step of Screening of CD90-positive Fibroblasts)

The fibroblasts may be screened in order to increase the ratio of CD90+ fibroblasts. By this screening, cardiomyocytes can be eliminated from the fibroblasts. Examples of the screening include cell sorting methods such as flow cytometry, the magnetic bead method, the affinity column method, and the panning method, using an anti-CD90 antibody. More specifically, for example, magnetic cell sorting (MACS) or fluorescence-activated cell sorting (FACS) may be used. The anti-CD90 antibody may be a commercially available product, or may be prepared by a known method. Either a monoclonal antibody or a polyclonal antibody may be used, but, from the viewpoint of specificity, a monoclonal antibody is preferably used. Alternatively, the screening may be carried out by introduction of a drug resistance gene for elimination of CD90-negative fibroblasts. Alternatively, a fluorescent protein-coding gene may be introduced, and then fluorescence protein-positive cells may be isolated by fluorescence-activated cell sorting (FACS) or the like.

(Step of Screening of Cells Having Adhesiveness)

The screening of fibroblasts may be carried out by utilization of a difference in the adhesiveness. Since CD90-positive fibroblasts have properties that allow their adherence to a culture dish which is uncoated (not subjected to coating with gelatin or the like), the purity of the fibroblasts can be increased by this step. More specifically, fibroblasts are plated on an uncoated culture dish, and culture is carried out for, for example, 2 hours, 4 hours, 6 hours, 8 hours, 12 hours, or 24 hours. By collecting the fibroblasts adhering to the culture dish, the screening can be carried out.

(Step of Screening of CD106+ Fibroblasts)

For inclusion of CD106+ fibroblasts in the injectable composition, fibroblasts are typically subjected to a step of screening of CD106+ fibroblasts. In cases where CD106+ fibroblasts can be obtained without performing such a step, this step may be omitted. Examples of the screening of CD106+ fibroblasts include cell sorting methods such as flow cytometry, the magnetic bead method, the affinity column method, and the panning method, using an anti-CD106 antibody (anti-VCAM-1 antibody). More specifically, for example, magnetic cell sorting (MACS) or fluorescence-activated cell sorting (FACS) may be used. The anti-CD106 antibody may be a commercially available product, or may be prepared by a known method. Alternatively, the screening may be carried out by introduction of a drug resistance gene for elimination of CD106-negative fibroblasts. Alternatively, a fluorescent protein-coding gene may be introduced, and then fluorescent protein-positive cells may be isolated by fluorescence-activated cell sorting (FACS) or the like. Either a monoclonal antibody or a polyclonal antibody may be used, but, from the viewpoint of specificity, a monoclonal antibody is preferably used. Alternatively, a method such as real-time PCR, next-generation sequencing, or in situ hybridization may be used to confirm expression of the CD106 gene in the cells, and then a CD106 gene-expressing group may be isolated.

(Culture Step)

The fibroblasts may be subjected to a culture step for the purpose of, for example, achieving a desired cell number, and/or allowing the cells to have a desired function. The culture conditions are not limited, and the culture may be carried out by a known cell culture method.

The culture medium used for the culture may be appropriately set depending on, for example, the type of the cells to be cultured. Examples of culture media that may be used include DMEM, α-MEM, HFDM-1(+), and RPMI-1640. Nutritional substances such as FCS and FBS; growth factors; cytokines; antibiotics; and the like may be added to the culture medium.

The number of days of the culture period may be appropriately set for the purpose of, for example, achieving a desired cell number, and/or allowing the cells to have a desired function. Examples of the culture period include periods such as 1 day, 2 days, 3 days, 4 days, 5 days, 6 days, 7 days, 8 days, 9 days, 10 days, 2 weeks, 1 month, 2 months, 3 months, and 6 months.

The culture temperature may be appropriately set depending on the type of the cells to be cultured. The culture temperature may be, for example, not less than 10° C., not less than 15° C., not less than 20° C., not less than 25° C., or not less than 30° C., and may be, for example, not more than 60° C., not more than 55° C., not more than 50° C., not more than 45° C., or not more than 40° C.

The culture step may be carried out a plurality of times. For example, the culture may be carried out each time when the purity of the desired fibroblasts is increased by screening.

(Collection Step)

The cultured fibroblasts are collected by a collection step. In the collection step, the cells may be detached using a protease such as trypsin, and then collected. Alternatively, a temperature-responsive culture dish may be used, and the cells may be detached by changing of the temperature, followed by collection of the cells.

In another embodiment of the present invention, a method for producing fibroblasts for treatment, which method comprises, among the above-described steps, the step of screening of CD106+ fibroblasts, may be provided.

Further, a method for producing fibroblasts for treatment, which method comprises, among the above-described steps, the step of screening of CD106+ fibroblasts and the step of screening of CD90+ fibroblasts, may be provided.

Further, a method for producing fibroblasts for treatment, which method comprises one, or an arbitrary combination of two or more, of the above-described steps, may be provided.

In another embodiment of the present invention, a method for treatment of a cardiac disease, which method comprises carrying out infusion of an injectable composition containing fibroblasts into a necrotic cardiac tissue region or a vicinity thereof, and/or into a coronary artery, or a vein, artery, lymph node, or lymph vessel, wherein the fibroblasts contain CD106+ fibroblasts, may be provided.

Further, use of fibroblasts as an injectable composition, wherein the fibroblasts contain CD106+ fibroblasts, may be provided.

In another embodiment, a planar or three-dimensional cellular tissue containing CD106+ fibroblasts may be provided. Although the CD106+ fibroblasts may be formed into a planar or three-dimensional cellular tissue after co-culture with another kind of cells such as cardiomyocytes, the CD106+ fibroblasts can effectively function as a planar or three-dimensional cellular tissue even without the co-culture. Examples of the planar or three-dimensional cellular tissue include, but are not limited to, cell sheets; cell fibers; and cellular tissues formed by a 3D printer.

Examples

The present invention is described below in more detail by way of Examples. However, the scope of the present invention is not limited thereby.

[Improvement of Cardiac Functions by Administration of CD106+ Mouse Fibroblasts]

<Animals and Reagents>

Wild-type C57BL/6 mice and wild-type Slc: SD rats were purchased from Japan SLC Inc. (Shizuoka, Japan).

The following antibodies were used for immunofluorescence staining and fluorescence-activated cell sorting (FACS): mouse monoclonal anti-CD106 (VCAM-1)-PE (Miltenyi Biotec, Bergisch Gladbach, Germany), rabbit polyclonal anti-connexin 43 (Cell signaling technology, MA), mouse monoclonal anti-vimentin (Abcam, Cambridge, UK), and Hoechst 33258 solution (St. Louis, Mich.).

A secondary antibody was purchased from Jackson Immuno Research Laboratories (West Grove, Pa.).

<Fibroblasts and Cardiomyocytes>

Mouse cardiac fibroblasts were obtained from a wild-type C57BL/6 mouse (neonate, 1 day old) according to a previous report (Matsuura K, et al., Biomaterials. 2011; 32:7355-7362). The cells obtained were cultured in high-glucose DMEM+10% FBS in a 10-cm culture dish. Three to five days after the beginning of the culture, the cells were detached with 0.05% trypsin/EDTA, and then subcultured in another 10-cm culture dish.

Cardiomyocytes (Cor.AT) derived from mouse embryonic stem cells (ES cells) were purchased from Axiogenesis AG (Cologne, Germany). Differentiation into cardiomyocytes, and purification of the cells were carried out according to the instructions.

<Fluorescence-Activated Cell Sorting (FACS) of CD106+ Mouse Cardiac Fibroblasts>

Mouse cardiac fibroblasts ($2 \times 10^7$ cells/experiment) were stained with a mouse anti-CD106 (VCAM-1)-PE antibody. The staining was carried out according to the instructions. CD106+ fibroblasts were separated by an S3e cell sorter (Bio-Rad, PA).

<Immunofluorescence Staining>

The cells were fixed with 4% paraformaldehyde, and then subjected to immunofluorescence staining, as described in a previous report (Matsuura K, et al., Biomaterials. 2011; 32:7355-7362). The stained sample was analyzed using IN Cell Analyzer 2200 (GE Healthcare, Buckinghamshire, UK) and IN Cell Developer Toolbox 1.9.2 (GE Healthcare).

<Surgical Treatment Procedure>

Rat heart failure was induced by occluding the left anterior descending coronary artery (LAD) for 30 minutes under inhalation anesthesia and then allowing reperfusion of blood flow. More specifically, first, male Slc: SD rats of 11 days to 12 weeks old were provided (369.0-506.5 g, Japan SLC Inc., Shizuoka). A mixture containing 0.15 mg/kg medetomidine hydrochloride, 2 mg/kg midazolam, and 2.5 mg/kg butorphanol tartrate was provided, and then diluted with physiological saline. The resulting dilution in a volume of 10 mL/kg was intraperitoneally administered to each rat for anesthetization, and then hair in the periphery of the chest was clipped and removed. After the hair removal, a tracheal tube was orally intubated, and artificial respiration was performed (tidal volume: 2.0 to 2.5 mL/stroke, breathing rate: 75 strokes/min.) using a respirator for small animals (model SN-480-7×2T, Shinano Manufacturing Co., Ltd.). Anesthesia was maintained with 2% isoflurane using an inhalation anesthesia apparatus (model KN-1071, Natsume Seisakusho Co., Ltd.), and the rat was fixed in a supine position or lateral position.

The incision site was disinfected with Isodine solution, and then lidocaine was sprayed for pain relief. The heart was exposed by thoracotomy in the lateral side of the chest, and atropine sulfate (0.02 mg/kg) was intramuscularly administered for prevention of arrhythmia, when necessary. Using an atraumatic needle (6-0 VICRYL) (Johnson & Johnson, NJ), the left anterior descending coronary artery (LAD) was occluded for 30 minutes. By monitoring of the electrocardiogram, the presence or absence of occlusion (occurrence of myocardial ischemia) was investigated based on elevation of the ST potential and whitening of cardiac muscle (visual observation). In cases where ventricular fibrillation (VF) appeared, resuscitation (direct stimulation of the heart using ring forceps) was performed to terminate the ventricular fibrillation. By allowing reperfusion of blood flow after 30 minutes of the occlusion, an ischemia-reperfusion model was prepared.

After the reperfusion, intramyocardial injection was performed. The chest was then closed, and sutured with an atraumatic needle (3-0 VICRYL) (Johnson & Johnson, NJ), followed by disinfection of the suture site with Isodine solution.

The rats were divided into the following four treatment groups.

(S1) Injection of CD106+ mouse fibroblasts and mouse cardiomyocytes (50 µL of high-glucose DMEM+10% New Born Calf Serum (NBCS) containing $4 \times 10^5$ fibroblasts and $1.6 \times 10^6$ cardiomyocytes)

(S2) Injection of CD106+ mouse fibroblasts (50 µL of high-glucose DMEM+10% NBCS containing $2 \times 10^6$ fibroblasts)

(S3) A group subjected to surgical treatment alone (S4) A group without surgical treatment The injection of the cells was carried out at two positions in the vicinity of the damaged region (25 µL/injection).

<Evaluation of Cardiac Functions>

For comparative evaluation of left ventricular functions of the prepared model rat, cardiac functions were monitored by performing cardiac ultrasonography (echocardiography) from Week 0 to Week 10 at two-week intervals after the injection of the cells.

Figure 4:
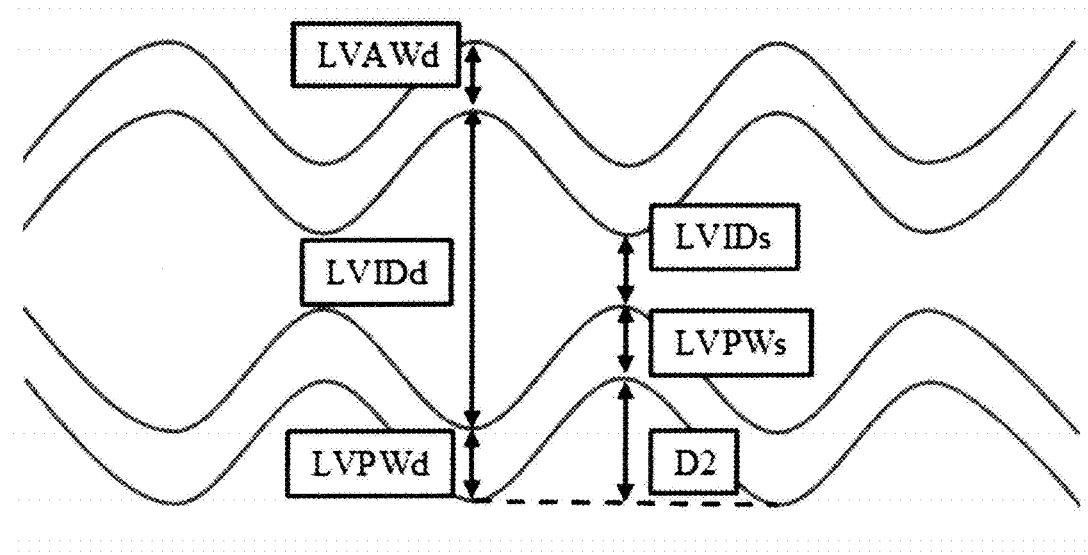
FIG. 4 shows a graph illustrating a heart function (the left ventricular fractional shortening (FS) and the left ventricular ejection fraction (EF)).

The cardiac ultrasonography (echocardiography) was carried out using an ultrasonic diagnostic apparatus (Nolus, Hitachi, Ltd.). More specifically, a superficial linear probe was placed on the chest of the rat, and measurement was carried out by M-mode for the left ventricular end-diastolic diameter (LVIDd), the left ventricular end-systolic diameter (LVIDs), the left ventricular anterior wall end-diastolic thickness (LVAWd), the left ventricular free wall end-diastolic thickness (LVPWd), and the left ventricular free wall end-systolic thickness (LVPWs). As the left ventricular end-diastolic volume (LVEDV) and the left ventricular end-systolic volume (LVESV), values automatically calculated by the echo apparatus were employed. Further, based on the drawn M-mode images, the displacement of the left ventricular epicardial surface (D2) was measured. An index for the left ventricular extensibility EMI=(LVPWs−LVPWd)/(LVPWs×D2) and its simplified index DWS=(LVPWs−LVPWd)/LVPWs were calculated. Further, according to the following equations and FIG. 4, the left ventricular fractional shortening (FS) and the left ventricular ejection fraction (EF) were calculated.

Left ventricular fractional shortening (FS)=(LVIDd−LVIDs)/LVIDd×100

Left ventricular ejection fraction (EF)=(LVEDV−LVESV)/LVEDV×100

<Histological Experiment>

The left ventricle of the heart removed was fixed by immersion in 10% buffered formalin solution. The left ventricle was divided in the short-axis direction into three portions such that the length in the long-axis direction between the position immediately below the ligation and the cardiac apex was equally divided into three parts. Each portion of cardiac muscle was embedded in one paraffin block such that the origin side is positioned in the embedded side. After preparation of thin slices, Masson trichrome staining was carried out. Images of the samples after the Masson trichrome staining were captured into an image analyzer (general-purpose image processor "Win ROOF Version 5.5", Mitani Corporation), and the myocardial infarction area (%) was measured for each of the three portions by the image analyzer.

<Statistical Analysis>

The evaluation results on cardiac functions are represented as mean±SE (standard error). All other data are represented as mean±SD (standard deviation). Variation difference among three or more groups was calculated by one-way analysis of variance. Subsequently, significant difference among the three groups was calculated by Tukey-Kramer Multiple Comparison Test. Significance of difference was assumed when the p-value was smaller than 0.05. All statistical calculations were carried out using Statcel software.

<Localization of VCAM-1 Protein Among Mouse Cardiac Fibroblasts>

Figure 1B:
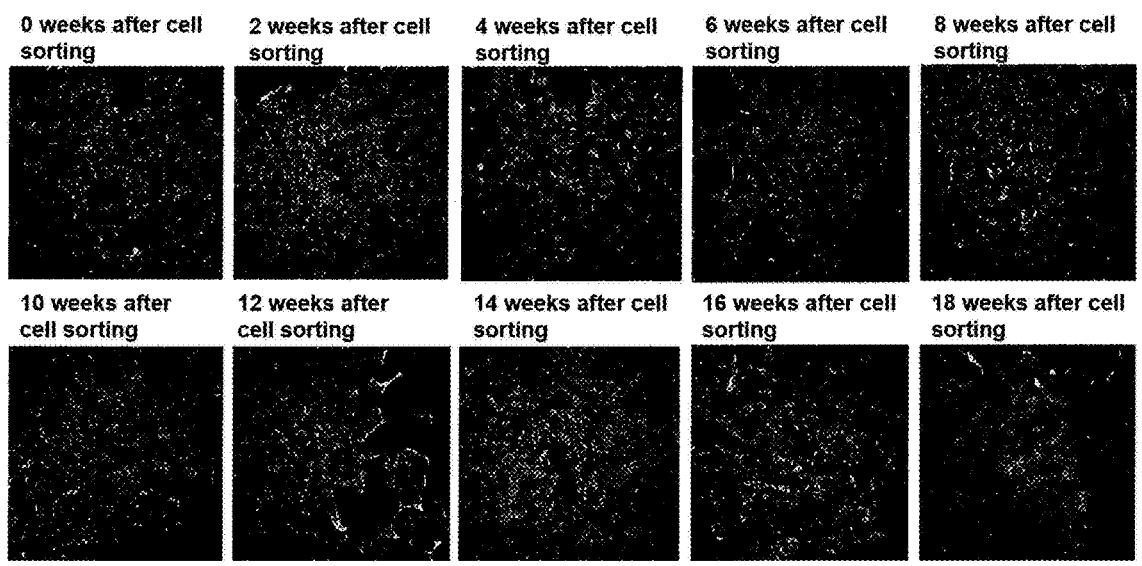
FIG. 1B shows VCAM-1-positive immunofluorescence images of CD106-positive mouse cardiac fibroblasts (drawing-substituting photographs).
Figure 1C:
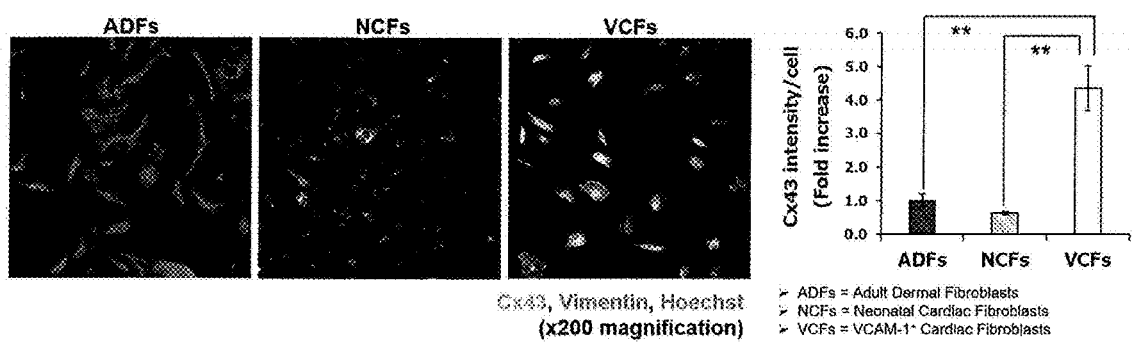
FIG. 1C shows connexin 43-positive immunofluorescence images of each type of fibroblasts (drawing-substituting photographs).

For separation of CD106+ fibroblasts, which improve the growth and the migration of cardiomyocytes, expression of VCAM-1 protein in mouse cardiac fibroblasts was investigated (FIG. 1A). The region of CD106+ fibroblasts was strictly selected for elimination of negative cells. About 39.2% of the cardiac fibroblasts were CD106+ fibroblasts. Subsequently, in order to evaluate whether or not CD106+ fibroblasts uniformly express VCAM-1 for a long period, the CD106+ fibroblasts were cultured in vitro until Week 18 to evaluate expression of VCAM-1 protein (FIG. 1B). In all CD106+ fibroblasts, high expression levels of VCAM-1 protein were maintained throughout the 18 weeks. Further, the CD106+ fibroblasts highly expressed connexin 43, that is, a gap junction protein for myocardial electrical network transmission (FIG. 1C). Based on these discoveries, it can be understood that CD106+ fibroblasts have an ability to continue expression of VCAM-1 protein, and to propagate electrical excitation of the heart.

<Improvement of Heart Functions by CD106+ Mouse Fibroblasts after Myocardial Infarction>

Figure 2A:
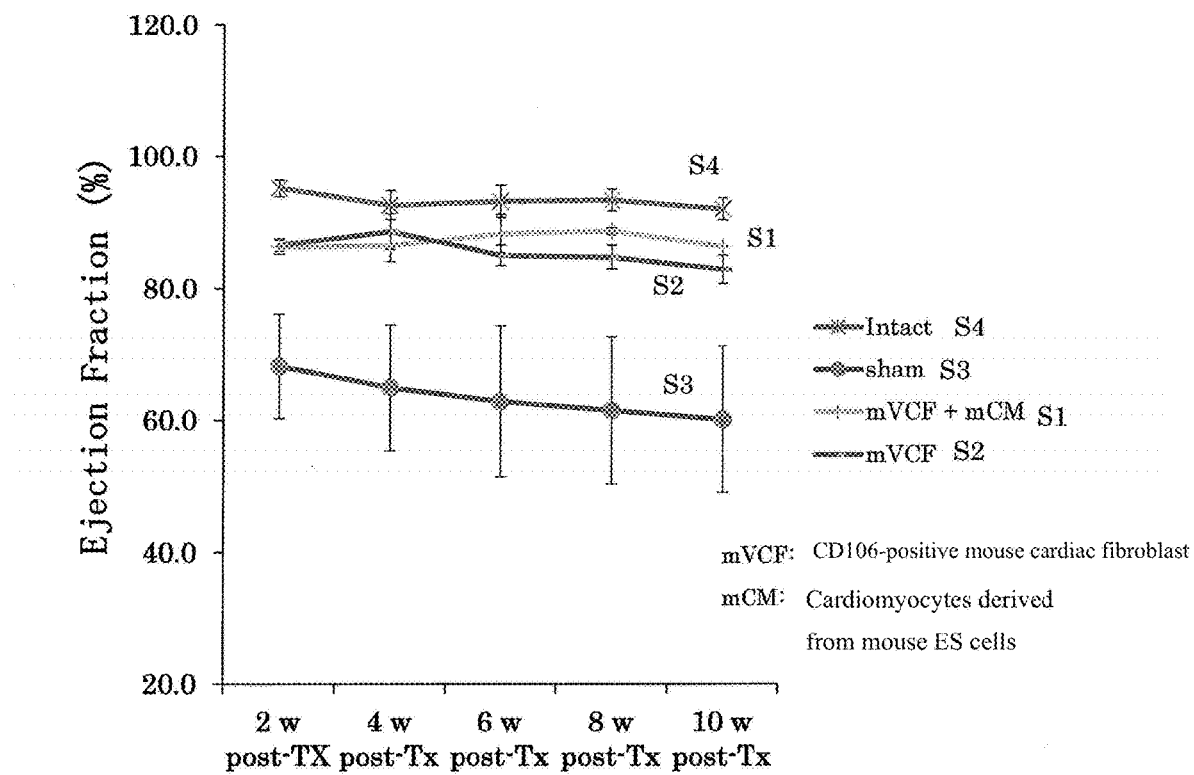
FIG. 2A shows a graph illustrating a heart function (Ejection Fraction, left ventricular ejection fraction) after injection of CD106-positive mouse cardiac fibroblasts.
Figure 2B:
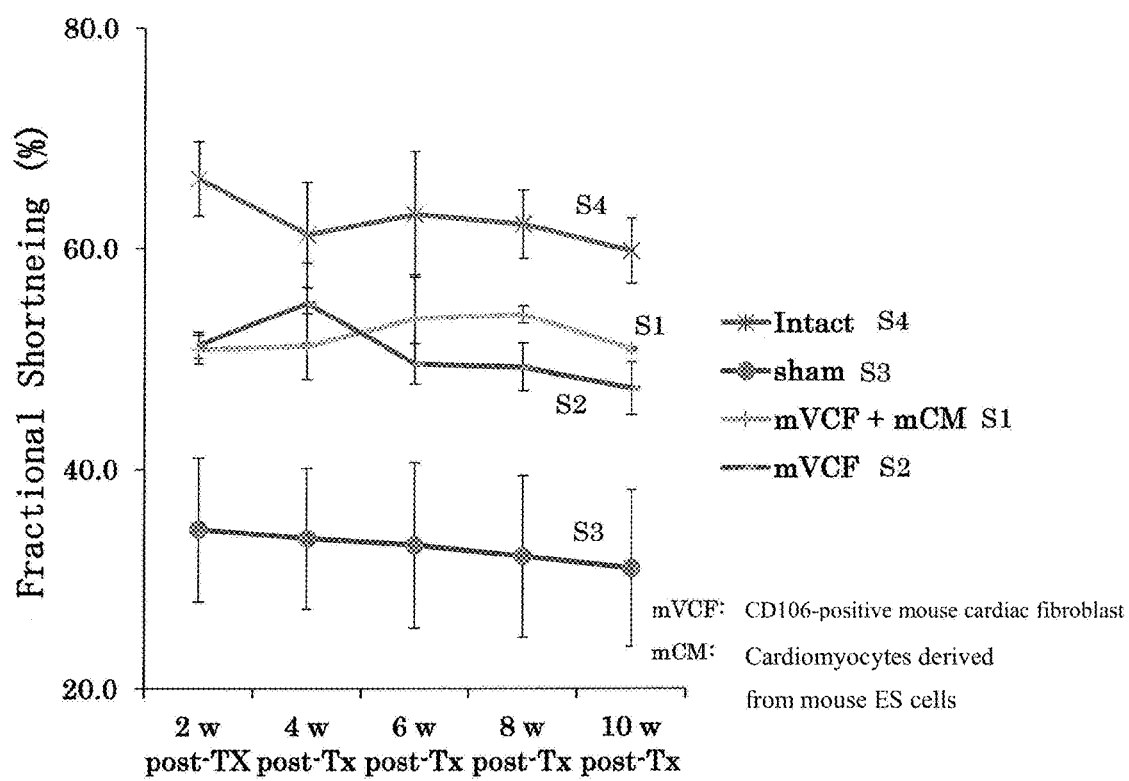
FIG. 2B shows a graph illustrating a heart function (Fractional Shortening, left ventricular fractional shortening) after injection of CD106-positive mouse cardiac fibroblasts.
Figure 2C:
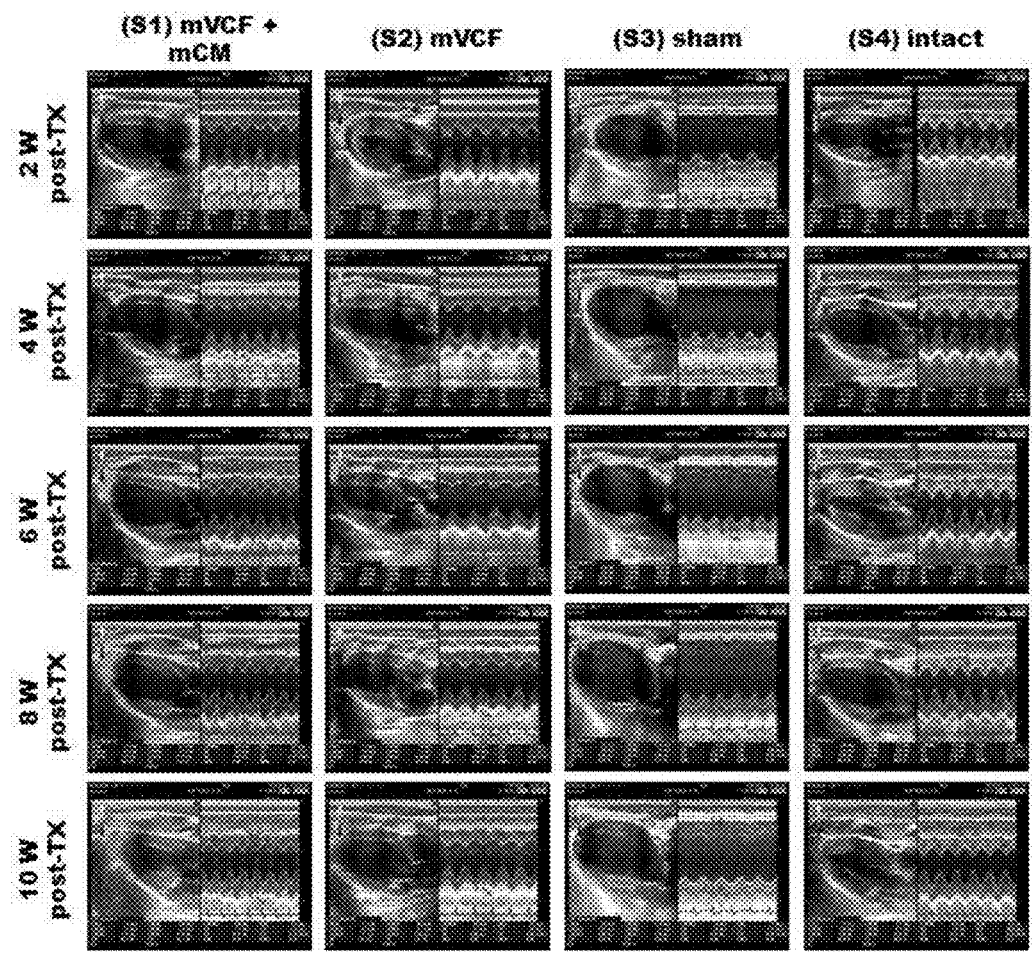
FIG. 2C shows echocardiographic images of rat hearts (drawing-substituting photographs).

According to echocardiography, at Week 2 to Week 10 after the injection, the S1 and S2 groups showed improvement in the left ventricular ejection fraction (EF) and the left ventricular fractional shortening (FS) compared to the S3 and S4 groups. On the other hand, there was no significant difference in EF or FS between the S1 and S2 groups (FIG. 1A, FIG. 2B). Thus, it can be understood that the administration of CD106+ fibroblasts caused improvement of the pumping ability of the heart damaged by the myocardial infarction. The presence of cardiomyocytes was not important for the composition of the injectable composition.

<Improvement of Collagenous Fibrotic Infarct Area by CD106+ Mouse Fibroblasts>

Figure 3A:
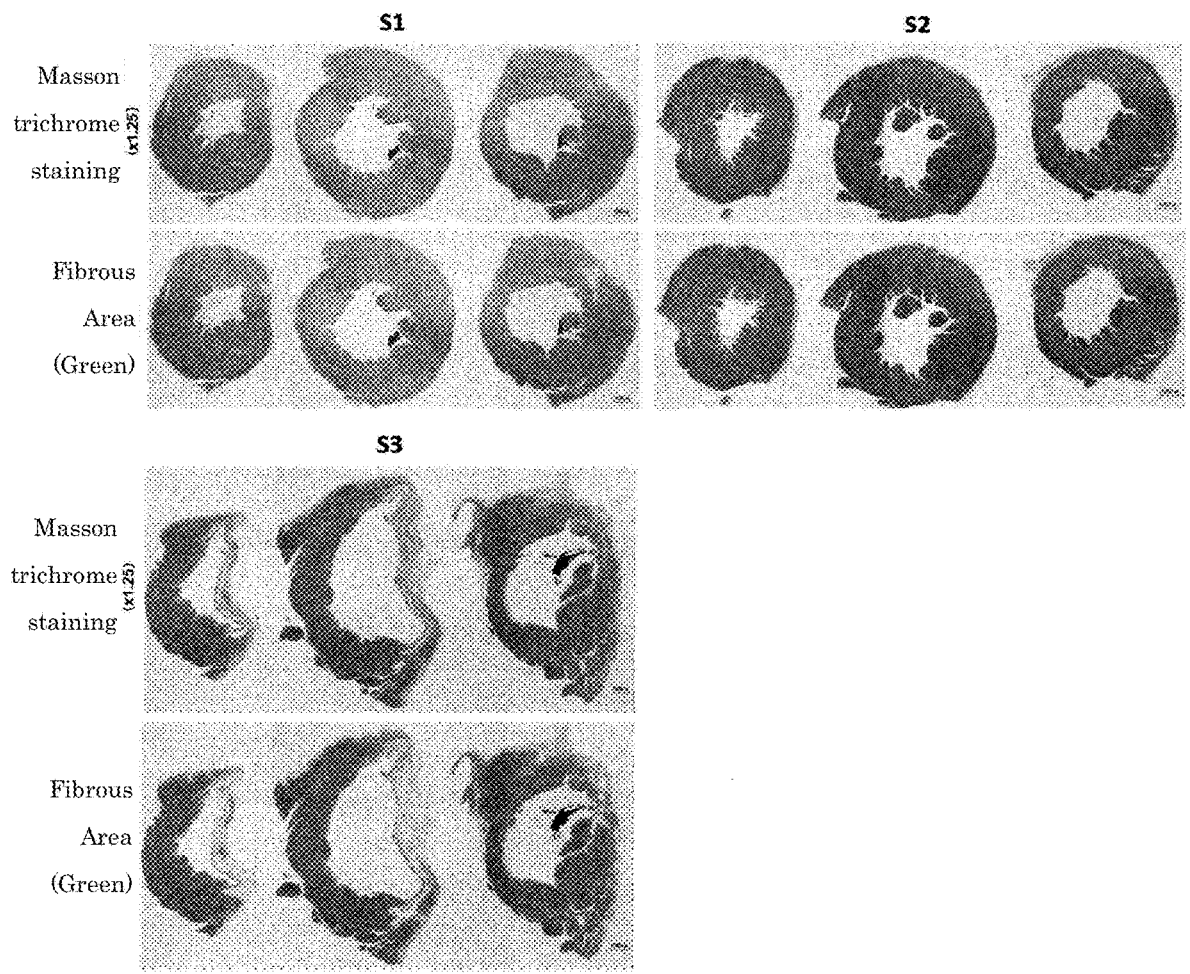
FIG. 3A shows images of collagenous fibrotic infarct areas in rat hearts (drawing-substituting photographs).
Figure 3B:
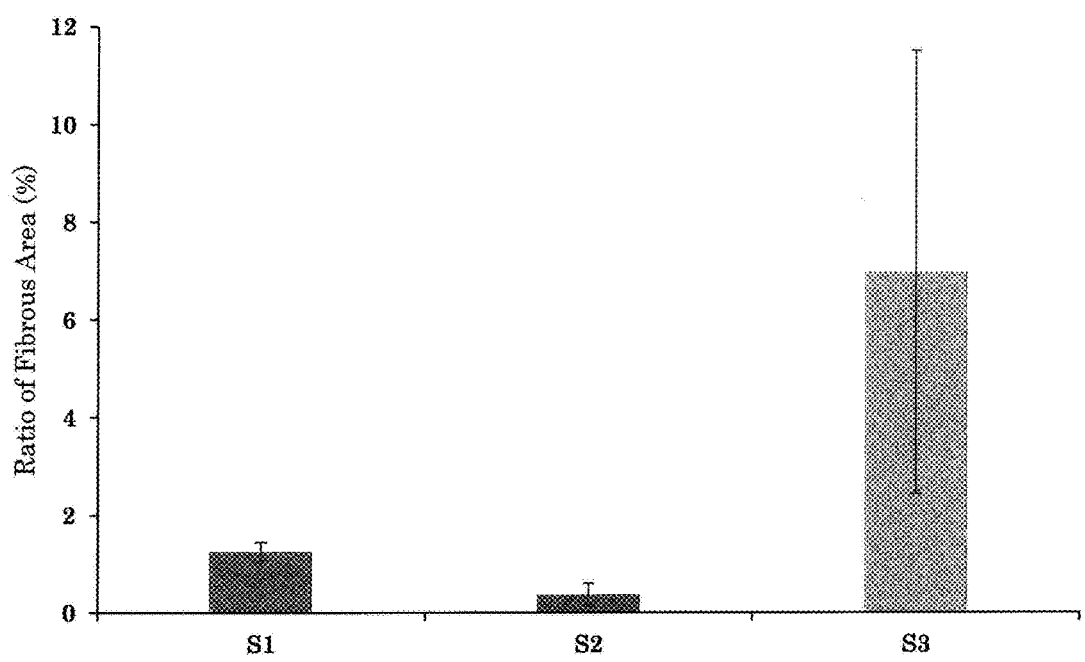
FIG. 3B shows a graph showing the areas of collagenous fibrotic infarct in rat hearts.

At Week 10 after the injection, a pathological tissue specimen of the heart was prepared, and subjected to Masson trichrome staining. As a result, it could be confirmed that the collagenous fibrotic infarct areas in the S1 and S2 groups were significantly small (FIG. 3A). Further, as a result of measurement of the area (%) of the collagenous fibrotic infarct using an image analyzing software, the area of fibrosis was found to be significantly small in S2 (FIG. 3B). Thus, it can be understood that the administration of CD106+ fibroblasts caused not only improvement of the systolic function of the heart damaged by myocardial infarction and the like, but also significant suppression of collagen fibrosis. The presence of cardiomyocytes was not important for the composition of the injectable composition.

By the above experiments, the importance of VCAM-1-positive fibroblasts for effective treatment of an ischemic heart disease was first demonstrated, and it can be understood that administration of CD106+ fibroblasts can produce a desirable result in treatment of a heart disease. Administration of VCAM-1-positive fibroblasts can be used in treatment for effective amelioration of an ischemic heart disease. Further, since remarkable improvement of cardiac functions and remarkable suppression of collagen fibrosis were found as a result of administration of cardiac fibroblasts expressing VCAM-1, it can be understood that the administration is effective also for treatment of other cardiac diseases.

[Improvement of Cardiac Functions by Administration of CD106+ Rat Fibroblasts]

Subsequently, improvement of cardiac functions by administration of CD106+ rat fibroblasts to rats was investigated.

<Fibroblasts and Cardiomyocytes>

From an Slc: SD fetal rat (embryonic day 20), the heart was collected, and its tissue was homogenized using gentle MACS (Miltenyi Biotec), followed by collecting rat cardiac fibroblasts based on the difference in the adhesiveness to the base culture-material surface. The cells obtained were cultured in high-glucose DMEM supplemented with 10% NBCS in a 10-cm culture dish. Three to five days after the beginning of the culture, the cells were detached with 0.05% trypsin/EDTA, and then subcultured in another 10-cm culture dish.

<Cell Sorting>

The cells were subjected to primary immunostaining with CD106 (VCAM-1)-Biotin antibodies, rat (Miltenyi Biotec), and then to secondary immunostaining with Anti-Biotin MicroBeads (Miltenyi Biotec). From the stained cells, CD106-positive cells alone were collected by autoMACS (Miltenyi Biotec) to provide CD106+ rat fibroblasts.

<Preparation and Echocardiographic Measurement of Chronic Heart Failure Rat Model>

Male nude rats (F344/N Jcl-rnu/rnu) of 8 weeks old were purchased from CLEA Japan, Inc. (Tokyo, Japan). After 1 week of acclimation, each animal was subjected to inhalation anesthesia with 2% isoflurane (anesthetic adjuvant; laughing gas:oxygen=7:3) using an inhalation anesthesia apparatus for experimental animals (Soft Lander (Shin-ei Industries, Inc., Saitama, Japan)), and then the hair was clipped. Immediately thereafter, tracheal intubation was carried out, and 0.5 to 2% isoflurane (anesthetic adjuvant; laughing gas:oxygen=7:3) inhalation anesthesia gas was directly introduced into the respirator to maintain anesthesia. Under artificial respiratory management, the animal was fixed in a supine position, and thoracotomy was performed by longitudinally cutting, at costal cartilage, two or three ribs between the left third rib and fifth rib. Using a retractor, the operative field was expanded, and the pericardial membrane was detached to expose the heart. The left atrium was lifted up, and a thread was passed at a depth of about 2 mm through a length of 4 to 5 mm in the left ventricle using an atraumatic weakly curved round needle for blood vessels (6-0: Nescosuture). Both ends of the thread were combined together, and a snare prepared with a polyethylene tube (PESO, Becton Dickinson) was passed therethrough. The thread was tightened using an artery clamp (snare method) to cause coronary artery ischemia for 30 minutes. Thereafter, reperfusion was carried out. After the conditions became stable, the absence of bleeding was confirmed, and chest drainage was carried out, followed by suture of the muscle layer and the skin. For the skin, subcuticular suture was performed. When normal suture was performed, suture removal was carried out depending on the postoperative conditions monitored. One week after the preparation of the model, that is, one day before the administration of the cells, echocardiographic measurement was carried out using an ultrasonic imaging diagnostic apparatus (Xario SSA-660A, Toshiba Medical Systems Corporation, Tochigi, Japan). Individuals having a left ventricular ejection fraction (LVEF=(LVIDd3−LVIDs3)/LVIDd3) of not more than 55% were regarded as a chronic heart failure model, and subjected to a CD106+ human fibroblast administration experiment.

<Administration of CD106+ Rat Fibroblasts to Chronic Heart Failure Rat Model>

On the day of the administration test, CD106+ rat fibroblasts were diluted with high-glucose DMEM+10% NBCS, and $2.0 \times 10^6$ cells/50 μL, in terms of the live cell number, of the cell suspension was administered to each individual. For a control, 50 μL of DMEM+10% NBCS alone was administered. Each group was provided with N=4.

While anesthesia was maintained by the same method as in the preparation of the model, the total amount, 50 μL, of the cell suspension was administered to the animal using a catheter with a 30-G needle dividedly at two positions in the infarct region under artificial respiratory management. After the conditions became stable, the absence of leakage of the administered liquid or bleeding was confirmed, and chest drainage was carried out, followed by suture of the muscle layer and the skin. For the skin, subcuticular suture was performed. When normal suture was performed, suture removal was carried out depending on the postoperative conditions monitored.

<Evaluation of Cardiac Functions of Chronic Heart Failure Model Rat by Echocardiography>

Figure 5:
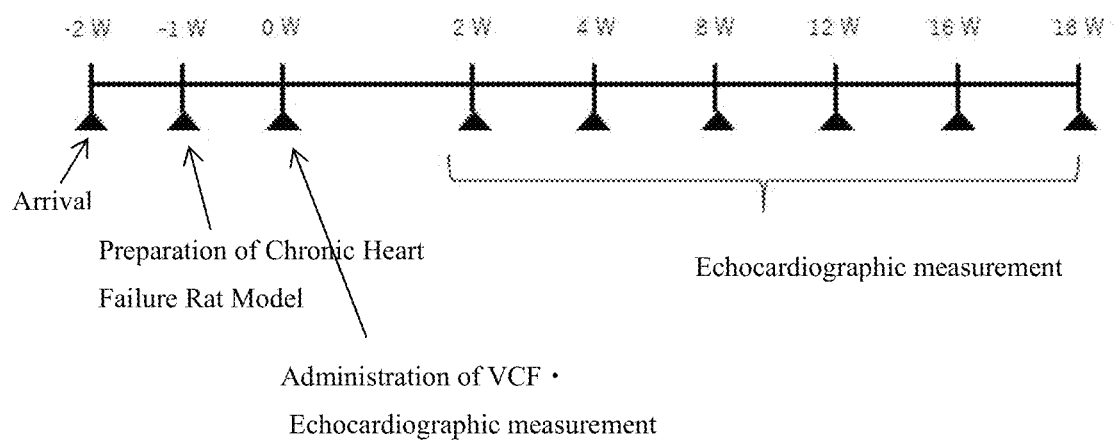
FIG. 5 shows a heart function follow-up schedule for a rat chronic heart failure model, which follow-up was carried out by echocardiography. For confirmation of the therapeutic effect of CD106-positive rat fibroblasts on chronic heart failure, follow-up of cardiac functions was carried out by echocardiography from the day of administration of the cells to Week 18 at two-week intervals.

The chronic heart failure model to which the CD106+ rat fibroblasts were administered was followed up while echocardiographic measurement was carried out using an ultrasonic imaging diagnostic apparatus (Xario SSA-660A, Toshiba Medical Systems Corporation, Tochigi, Japan) according to the schedule shown in FIG. 5. More specifically, hair on the chest of the animal was clipped with a hair clipper, and a probe was placed on the chest to measure the following items by M-mode. As main items, the left ventricular ejection fraction (LVEF=(LVIDd3−LVIDs3)/LVIDd3), the left ventricular fractional shortening (LVFS=(LVIDd−LVIDs)×100/LVIDd), the left ventricular end-diastolic volume (LVEDV), and the left ventricular end-systolic volume (LVESV) were measured. As sub-items, the left ventricular end-diastolic diameter (LVIDd), the left ventricular end-systolic diameter (LVIDs), the left ventricular anterior wall end-diastolic thickness (LVAWd=IVSTd), the left ventricular posterior wall end-diastolic thickness (LVPWTd), and the heart rate (HR) were measured. The cardiac function values except HR are expressed to one decimal place (by rounding to one decimal place), and HR, which is a sub-item, is expressed to two decimal places (by rounding to two decimal places).

[Improvement of Cardiac Functions by Administration of CD106+ Human Fibroblasts]

Subsequently, improvement of cardiac functions by administration of CD106+ human fibroblasts to rats or pigs was investigated.

<Cells and Antibodies>

Cardiac fibroblasts were purchased from the following manufacturers.

Caucasian fetal (21st week) heart-derived fibroblasts (c21wFCF, Cell Applications, San Diego, Calif.)

Caucasian adult (50's) heart-derived fibroblasts (c50yACF, Cell Applications, San Diego, Calif.)

Black adult (60's) heart-derived fibroblasts (b60yACF, Lonza, Basel, Switzerland)

<Cell Sorting>

The cells were subjected to primary immunostaining with CD106 (VCAM-1)-Biotin antibodies, human (Miltenyi Biotec), and then to secondary immunostaining with Anti-Biotin MicroBeads (Miltenyi Biotec). From the stained cells, CD106-positive cells alone were collected by autoMACS (Miltenyi Biotec) to provide CD106+ human fibroblasts.

Antibodies were purchased from the following manufacturers.

BV421 Rat IgG2a, Isotype Control RUO (BD Biosciences)
PE-REA Control (S) Isotype Control (Miltenyi Biotec)
Oct3/4-PE (Miltenyi Biotec)
Nanog-PE (Miltenyi Biotec)
Sox2-PE (Miltenyi Biotec)
Rabbit polyclonal anti-connexin 43 (Cell signaling technology)
Human STRO-1 Alexa Fluor 488-conjugated Antibody (R&D Systems, Minneapolis, Minn.)

All other antibodies were purchased from Abcam.

A secondary antibody was purchased from Jackson Immuno Research Laboratories.

For the antibodies that recognize a cell membrane surface protein, the cells were fixed with 4% paraformaldehyde, and then immunofluorescence staining was carried out. For Oct3/4-PE, Nanog-PE, and Sox2-PE, the CD106+ human fibroblasts were subjected to cell membrane permeabilization treatment with 0.1% Triton-X (Sigma Aldrich, St. Louis, Mo.) for 30 minutes (room temperature), and then immunofluorescence staining was carried out.

<Flow Cytometry>

The cells after the immunofluorescence staining were prepared into a density of $1.0 \times 10^6$ cells/per trial, and then analyzed with a flow cytometer (MACSQuant, Miltenyi Biotec). After recognition of the cellular area with FSC-A and SSC-A, the positive cell ratio (%, in terms of the cell number) for each marker protein was evaluated.

<Preparation and Echocardiographic Measurement of Chronic Heart Failure Rat Model>

By the same method as described above, a chronic heart failure model was prepared, and echocardiographic measurement was carried out.

<Administration of CD106+ Human Fibroblasts to Chronic Heart Failure Rat Model>

On the day of the administration test, CD106+ human fibroblasts were diluted with high-glucose DMEM+10% NBCS, and $2.0 \times 10^6$ cells/50 μL or $5.0 \times 10^5$ cells/50 μL, in terms of the live cell number, of the cell suspension was administered to each individual. Each group was provided with N=4. The maintenance of anesthesia in each animal, the cell administration method, and the suture and suture removal were carried out by the same methods as described above.

<Evaluation of Cardiac Functions of Chronic Heart Failure Model Rat by Echocardiography>

Figure 6:
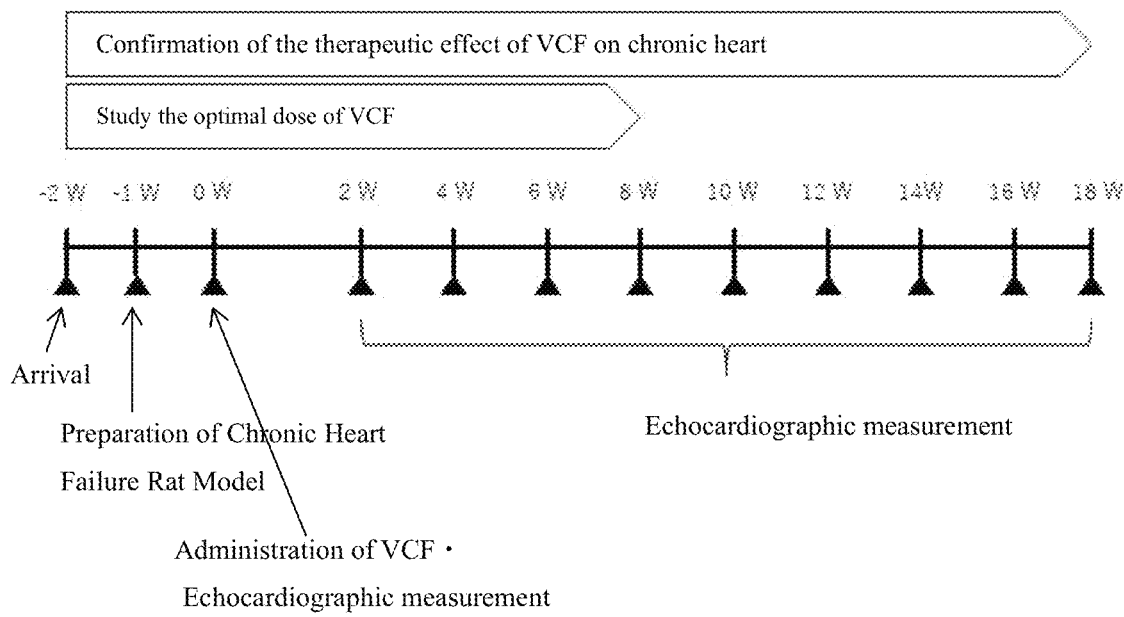
FIG. 6 shows a cardiac function follow-up schedule for a rat chronic heart failure model, which follow-up was carried out by echocardiography. For confirmation of the therapeutic effect of CD106-positive human fibroblasts on chronic heart failure, follow-up of cardiac functions was carried out by echocardiography from the day of administration of the cells to Week 18 at two-week intervals. For studying the optimal dose of CD106-positive human fibroblasts, follow-up of cardiac functions was carried out by echocardiography from the day of administration of the cells to Week 8 at two-week intervals. For providing a control, follow-up of heart functions by echocardiography was carried out at Week 2, Week 4, Week 8, Week 12, Week 16, and Week 18 after administration of a medium.

The chronic heart failure model to which the CD106+ human fibroblasts were administered was followed up while echocardiographic measurement was carried out using an ultrasonic imaging diagnostic apparatus (Xario SSA-660A, Toshiba Medical Systems Corporation, Tochigi, Japan) at two-week intervals according to the schedule shown in FIG. 6. The concrete method was the same as described above.

<Preparation and Echocardiographic Measurement of Chronic Heart Failure Pig Model>

SPF domesticated pigs of the LWD strain, 35 to 40 kg, were purchased (Okayama JA Livestock Co., Ltd., Okayama, Japan). A pig heart failure model was prepared by inflating the left anterior descending branch periphery for 60 minutes using a balloon catheter, and then, after an interval of 30 minutes, inflating the intermediate portion of the left anterior descending branch again for 60 minutes.

One week after the preparation of the model, that is, one day before the administration of the cells, echocardiographic measurement was carried out using MRI. Individuals having a left ventricular ejection fraction (EF) of less than 45% were regarded as a chronic heart failure model, and subjected to a CD106+ human fibroblast administration experiment.

<Administration of CD106+ Human Fibroblasts to Chronic Heart Failure Pig Model>

After induction of anesthesia, the pig heart failure model prepared was fixed on an operating table in a supine position. In the same manner as in the preparation of the above chronic heart failure pig model, a 6 Fr sheath was inserted from the groin, and a 6 Fr guiding catheter, preceded by a 0.035-inch guide wire, was inserted into the ascending aorta portion. The 0.035-inch guide wire was removed, and then air in the guiding catheter was removed, followed by allowing engagement in the left main trunk. After the engagement, confirmatory imaging was carried out at the median and LAO 30° angles to confirm the state of the coronary artery. Along a 0.014-inch guide wire, a microcatheter was inserted into the position immediately after the ostial portion of the left anterior descending branch. A 50-mL syringe preliminarily filled with CD106+ human fibroblasts ($2.0 \times 10^7$ cells/ 40 mL) was set to a syringe pump, and then connected to the inserted microcatheter, followed by performing administration at a flow rate of 1 mL/min. for 40 minutes. After the administration of the cells, 5 mL of physiological saline was administered at the same flow rate to perform flushing of the microcatheter. After completion of all administrations, the catheter and the sheath were removed. After pressure hemostasis at the sheath insertion site, the pig was allowed to recover from anesthesia, and returned into the cage. The administration of CD106+ human fibroblasts was carried out with N=1.

<Evaluation of Cardiac Functions of Chronic Heart Failure Model Pig by MRI>

The pig was subjected to an MRI scan before the day of administration of cells, four weeks after the administration, and eight weeks after the administration. The pig, under deep anesthesia, was placed on an examining table in an MRI room. In a supine position, the pig was connected with piping of an anesthesia apparatus and a tracheal tube. An electrocardiogram electrode was attached to the chest. A coil was fitted such that the coil covered the chest, and the pig was placed in the cylinder of the MRI body (Signa EXCITE XI TwinSpeed 1.5T Ver.11.1, GE Healthcare), followed by performing imaging. More specifically, first, cine MRI was used for 2D Fiesta imaging of an area that covers the heart along a body axis cross-section (Axial cross-section). Subsequently, from the data obtained, 2D Fiesta imaging of 20 slices per heartbeat was carried out at a cross-section that passes through the cardiac apex and the long axis of the left ventricle. From the imaging data, slices in the diastolic phase were selected, and 2D Fiesta imaging was carried out at a long-axis cross-section that passes through the cardiac apex and the vicinity of the mitral valve. Further, slices in the diastolic phase were selected, and 2D Fiesta imaging was carried out at a cross-section perpendicular to the long axis of the left ventricle at intervals of 6- to 8-mm width for 10 to 12 slices from the cardiac apex (short-axis cross-sections). The data obtained by the imaging were analyzed using a software application Cardiac VX. As evaluation items of cardiac functions, LVEF (left ventricular ejection fraction, %), SV (stroke volume, mL), EDV (end-diastolic volume, mL), and ESV (end-systolic volume, mL) were calculated. As indices related to rates, HR (heart rate, bpm), PFR (peak filling rate, mL/s), and PER (peak ejection rate, mL/s) were calculated. In addition, Mass ED (g), Cardiac Output (L/min), Mass (g), Mass ES (g), End-Diastolic Epicardial Volume (mL), and End-Systolic Epicardial Volume (mL) were calculated.

Further, Myocardial temporal change analysis Perfusion and LGE analysis were carried out for quantitative calculation of the infarct/fibrotic area present in the abnormal site of cardiac muscle. In the myocardial temporal change analysis Perfusion, first, a contrast agent (Omniscan intravenous injection 32% for intravenous injection) was intravenously administered from a vein route (intravenous) by bolus injection, and the process of first passing of the contrast agent through cardiac muscle was imaged (short-axis cross-section). The data obtained by the imaging were analyzed using a software application Cardiac VX. In the LGE analysis, first, a contrast agent (Omniscan intravenous injection 32% for intravenous injection, 0.25 mL/kg) was intravenously administered. Fast GRE imaging was then carried out 10 to 20 minutes thereafter (short-axis cross-section). The data obtained by the imaging were analyzed using a software application Cardiac VX. Since infarct areas and fibrotic areas appear with high signals, their differences from normal areas were quantitatively calculated by Region Of Interest (ROI) analysis. Similarly to the left ventricular function analysis, measurement was automatically carried out for several particular points. However, when it seemed that the measurement was carried out for a clearly wrong area, modification was applied. The ratio of infarct sites in the cardiac muscle tissue was also represented as a percentage.

<Statistical Analysis>

Data of in vitro tests are represented as mean±SD (standard deviation). Data of in vivo tests are represented as mean±SE (standard error). Significant difference between two groups was calculated by student's t-test. Variation difference among three or more groups was calculated by one-way analysis of variance. Subsequently, significant difference among the three groups was calculated by Tukey- Kramer Multiple Comparison Test. Significance of difference was assumed when the p-value was smaller than 0.05.

The experimental results were as follows.

<Therapeutic Effect of CD106+ Rat Fibroblasts on Rat Chronic Heart Failure Model>

Figure 7:
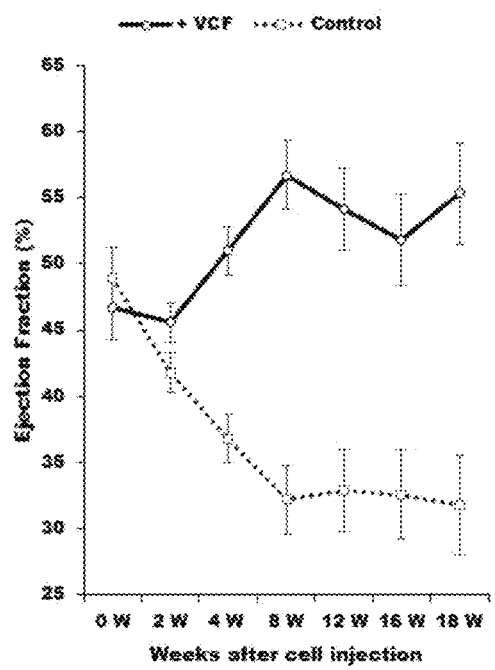
FIG. 7 shows the effect of administration of CD106-positive rat fibroblasts ($2.0 \times 10^6$ cells/50 µL) on recovery of cardiac functions in a rat chronic heart failure model. (A) represents the left ventricular ejection fraction (LVEF=(LVIDd3−LVIDs3)/LVIDd3); (B) represents the left ventricular fractional shortening (LVFS=(LVIDd−LVIDs)×100/LVIDd); (C) represents the left ventricular end-diastolic volume (LVEDV); and (D) represents the left ventricular end-systolic volume (LVESV). N=4.
Figure 7:
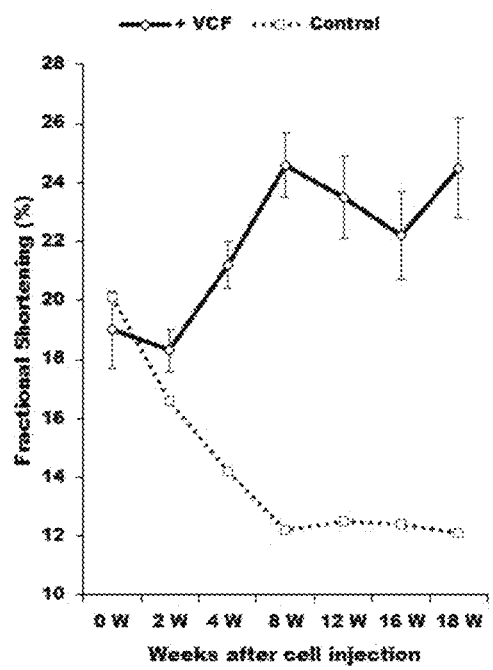
Figure 7:
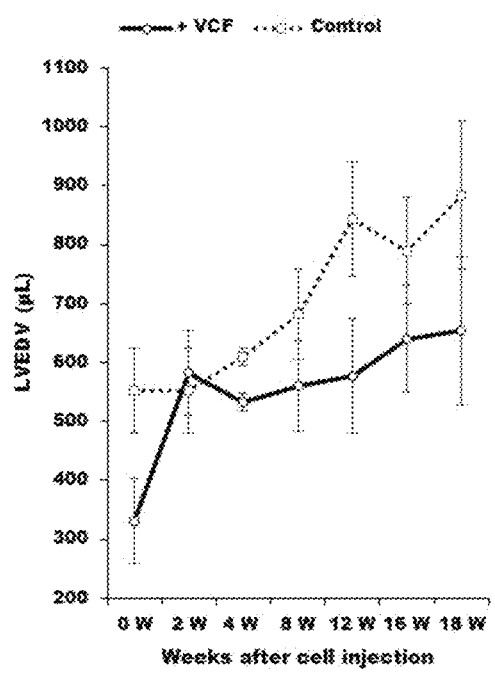
Figure 7:
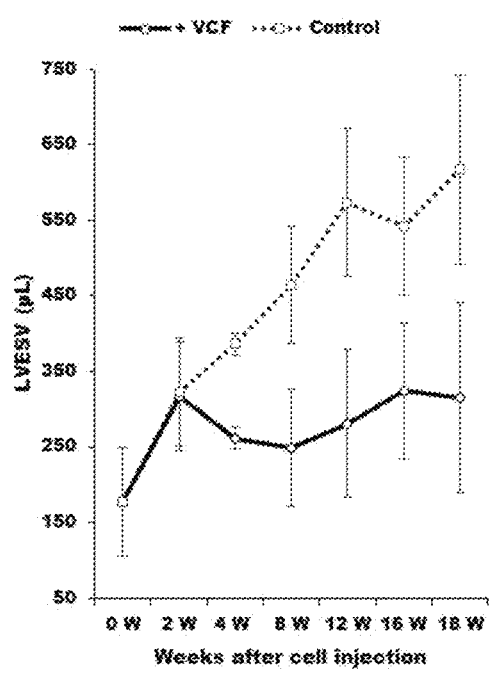

The CD106+ rat fibroblasts collected after the cell sorting were intramyocardially administered to the rat chronic heart failure model, and the effect on recovery from chronic heart failure was evaluated for 18 weeks after the administration of the cells. The results are shown in FIG. 7. The group in which the CD106+ rat fibroblasts were administered was found to show 32.9% improvement of EF and 12.4% improvement of FS compared to the control, at Week 18 after the administration. Neither an extreme increase/decrease in LVEDV nor an increase in LVESV was found throughout the 18 weeks after the administration. The results for the main items (LVEF, LVFS, LVEDV, and LVESV) and the results for the sub-items (LVIDd, LVIDs, IVSTd, LVPWTd, and HR) are shown in Tables 1 to 9.

TABLE 1

Trend of Left Ventricular Ejection Fraction (LVEF) of the Rat Heart Failure Model by Administration of the CD106+ Rat Fibroblasts (represented as "VCF" in the table)

| Groups | Animal Number | LVEF (%) at each week after cell injection | | | | | | |
|---|---|---|---|---|---|---|---|---|
| | | 0 W | 2 W | 4 W | 8 W | 12 W | 16 W | 18 W |
| +VCF | 106 | 53.20 | 43.60 | 54.50 | 65.60 | 67.10 | 67.10 | 68.20 |
| | 107 | 42.60 | 46.70 | 49.60 | 49.70 | 34.00 | 31.60 | 27.10 |
| | 108 | 46.90 | 46.10 | 50.20 | 50.50 | 50.80 | 57.50 | 63.20 |
| | 109 | 44.20 | 45.80 | 49.60 | 61.00 | 64.30 | 50.80 | 62.60 |
| | Mean | 46.70 | 45.60 | 51.00 | 56.70 | 54.10 | 51.80 | 64.70 |
| | S.E. | 2.30 | 0.70 | 1.20 | 3.90 | 7.60 | 7.50 | 1.80 |

TABLE 1-continued

Trend of Left Ventricular Ejection Fraction (LVEF) of the Rat Heart Failure Model by Administration of the CD106+ Rat Fibroblasts (represented as "VCF" in the table)

| Groups | Animal Number | LVEF (%) at each week after cell injection | | | | | | |
|---|---|---|---|---|---|---|---|---|
| | | 0 W | 2 W | 4 W | 8 W | 12 W | 16 W | 18 W |
| control | 101 | 50.90 | 42.50 | 41.60 | 39.10 | 42.00 | 42.60 | 43.00 |
| | 102 | 49.40 | 43.90 | 36.10 | 33.20 | 31.80 | 30.60 | 28.20 |
| | 103 | 42.10 | 37.50 | 32.70 | 27.70 | 29.30 | 29.90 | 29.30 |
| | 104 | 53.20 | 43.40 | 36.60 | 28.70 | 28.60 | 27.10 | 26.50 |
| | Mean | 48.90 | 41.80 | 36.80 | 32.20 | 32.90 | 32.60 | 31.80 |
| | S.E. | 2.40 | 1.50 | 1.80 | 2.60 | 3.10 | 3.40 | 3.80 |

TABLE 2

Trend of Left Ventricular Fractional Shortening (LVFS) of the Rat Heart Failure Model by Administration of the CD106+ Rat Fibroblasts (represented as "VCF" in the table)

| Groups | Animal Number | LVFS (%) at each week after cell injection | | | | | | |
|---|---|---|---|---|---|---|---|---|
| | | 0 W | 2 W | 4 W | 8 W | 12 W | 16 W | 18 W |
| +VCF | 106 | 22.30 | 17.40 | 23.10 | 30.00 | 31.00 | 31.00 | 31.70 |
| | 107 | 16.90 | 18.90 | 20.50 | 20.50 | 12.90 | 11.90 | 10.00 |
| | 108 | 19.00 | 18.60 | 20.70 | 20.90 | 21.10 | 24.80 | 28.40 |
| | 109 | 17.60 | 18.40 | 20.40 | 27.00 | 29.10 | 21.00 | 27.90 |
| | Mean | 19.00 | 18.30 | 21.20 | 24.60 | 23.50 | 22.20 | 24.50 |
| | S.E. | 1.20 | 0.30 | 0.60 | 2.30 | 4.10 | 4.00 | 4.90 |
| control | 101 | 21.10 | 16.90 | 16.40 | 15.20 | 16.60 | 16.90 | 17.10 |
| | 102 | 20.30 | 17.50 | 13.90 | 12.60 | 12.00 | 11.50 | 10.50 |
| | 103 | 16.60 | 14.50 | 12.40 | 10.30 | 10.90 | 11.20 | 10.90 |
| | 104 | 22.50 | 17.30 | 14.10 | 10.70 | 10.60 | 10.00 | 9.70 |
| | Mean | 20.10 | 16.60 | 14.20 | 12.20 | 12.50 | 12.40 | 12.10 |
| | S.E. | 1.30 | 0.70 | 0.80 | 1.10 | 1.40 | 1.50 | 1.70 |

TABLE 3

Trend of Left Ventricular End-Diastolic Volume (LVEDV) of the Rat Heart Failure Model by Administration of the CD106+ Rat Fibroblasts (represented as "VCF" in the table)

| Groups | Animal Number | LVEDV (μL) at each week after cell injection | | | | | | |
|---|---|---|---|---|---|---|---|---|
| | | 0 W | 2 W | 4 W | 8 W | 12 W | 16 W | 18 W |
| +VCF | 106 | 316.00 | 580.00 | 516.00 | 375.00 | 471.00 | 471.00 | 531.00 |
| | 107 | 235.00 | 614.00 | 564.00 | 825.00 | 804.00 | 825.00 | 890.00 |
| | 108 | 305.00 | 471.00 | 402.00 | 457.00 | 516.00 | 668.00 | 614.00 |
| | 109 | 471.00 | 668.00 | 649.00 | 580.00 | 516.00 | 597.00 | 580.00 |
| | Mean | 331.80 | 583.30 | 532.80 | 559.30 | 576.80 | 640.30 | 653.80 |
| | S.E. | 49.80 | 41.60 | 51.50 | 98.10 | 76.50 | 73.80 | 80.60 |
| control | 101 | 442.00 | 442.00 | 580.00 | 501.00 | 564.00 | 531.00 | 516.00 |
| | 102 | 668.00 | 668.00 | 649.00 | 868.00 | 1006.00 | 935.00 | 982.00 |
| | 103 | 686.00 | 686.00 | 597.00 | 632.00 | 868.00 | 804.00 | 1080.00 |
| | 104 | 415.00 | 415.00 | 614.00 | 724.00 | 935.00 | 890.00 | 959.00 |
| | Mean | 552.80 | 552.80 | 610.00 | 681.30 | 843.30 | 790.00 | 884.30 |
| | S.E. | 72.00 | 72.00 | 14.70 | 77.30 | 97.30 | 90.50 | 125.50 |

TABLE 4

Trend of Left Ventricular End-Systolic Volume (LVESV) of the Rat Heart Failure Model by Administration of the CD106+ Rat Fibroblasts (represented as "VCF" in the table)

| Groups | Animal Number | LVESV (μL) at each week after cell injection | | | | | | |
|---|---|---|---|---|---|---|---|---|
| | | 0 W | 2 W | 4 W | 8 W | 12 W | 16 W | 18 W |
| +VCF | 106 | 148.00 | 327.00 | 235.00 | 129.00 | 155.00 | 155.00 | 169.00 |
| | 107 | 135.00 | 327.00 | 284.00 | 415.00 | 531.00 | 564.00 | 649.00 |

TABLE 4-continued

Trend of Left Ventricular End-Systolic Volume (LVESV) of the Rat Heart Failure Model by Administration of the CD106+ Rat Fibroblasts (represented as "VCF" in the table)

| Groups | Animal Number | LVESV (μL) at each week after cell injection | | | | | | |
|---|---|---|---|---|---|---|---|---|
| | | 0 W | 2 W | 4 W | 8 W | 12 W | 16 W | 18 W |
| | 108 | 162.00 | 254.00 | 200.00 | 226.00 | 254.00 | 284.00 | 226.00 |
| | 109 | 263.00 | 362.00 | 327.00 | 226.00 | 184.00 | 294.00 | 217.00 |
| | Mean | 177.00 | 317.50 | 261.50 | 249.00 | 281.00 | 324.30 | 315.30 |
| | S.E. | 29.20 | 22.70 | 27.80 | 59.90 | 85.90 | 86.00 | 112.00 |
| control | 101 | 155.00 | 254.00 | 339.00 | 305.00 | 327.00 | 305.00 | 294.00 |
| | 102 | 217.00 | 375.00 | 415.00 | 580.00 | 686.00 | 649.00 | 705.00 |
| | 103 | 217.00 | 429.00 | 402.00 | 457.00 | 614.00 | 564.00 | 764.00 |
| | 104 | 123.00 | 235.00 | 389.00 | 516.00 | 668.00 | 649.00 | 705.00 |
| | Mean | 178.00 | 323.30 | 386.30 | 464.50 | 573.80 | 541.80 | 617.00 |
| | S.E. | 23.40 | 46.90 | 16.60 | 58.80 | 83.70 | 81.40 | 108.60 |

TABLE 5

Trend of Left Ventricular End-Diastolic Diameter (LVIDd) of the Rat Heart Failure Model by Administration of the CD106+ Rat Fibroblasts (represented as "VCF" in the table)

| Groups | Animal Number | LVIDd (mm) at each week after cell injection | | | | | | |
|---|---|---|---|---|---|---|---|---|
| | | 0 W | 2 W | 4 W | 8 W | 12 W | 16 W | 18 W |
| +VCF | 106 | 6.81 | 8.34 | 8.02 | 7.21 | 7.78 | 7.78 | 8.10 |
| | 107 | 6.17 | 8.50 | 8.26 | 9.38 | 9.30 | 9.38 | 9.62 |
| | 108 | 6.73 | 7.78 | 7.38 | 7.70 | 8.02 | 8.74 | 8.50 |
| | 109 | 7.78 | 8.74 | 8.66 | 8.34 | 8.02 | 8.42 | 8.34 |
| | Mean | 6.87 | 8.34 | 8.08 | 8.16 | 8.28 | 8.58 | 8.64 |
| | S.E. | 0.33 | 0.20 | 0.27 | 0.47 | 0.34 | 0.33 | 0.34 |
| control | 101 | 6.81 | 7.62 | 8.34 | 7.94 | 8.26 | 8.10 | 8.02 |
| | 102 | 7.54 | 8.74 | 8.66 | 9.54 | 10.02 | 9.78 | 9.94 |
| | 103 | 7.21 | 8.82 | 8.42 | 8.58 | 9.54 | 9.30 | 10.26 |
| | 104 | 6.41 | 7.46 | 8.50 | 8.98 | 9.78 | 9.62 | 9.86 |
| | Mean | 6.99 | 8.16 | 8.48 | 8.76 | 9.40 | 9.20 | 9.52 |
| | S.E. | 0.24 | 0.36 | 0.07 | 0.34 | 0.39 | 0.38 | 0.51 |

TABLE 6

Trend of Left Ventricular End-Systolic Diameter (LVIDs) of the Rat Heart Failure Model by Administration of the CD106+ Rat Fibroblasts (represented as "VCF" in the table)

| Groups | Animal Number | LVIDs (mm) at each week after cell injection | | | | | | |
|---|---|---|---|---|---|---|---|---|
| | | 0 W | 2 W | 4 W | 8 W | 12 W | 16 W | 18 W |
| +VCF | 106 | 5.29 | 6.89 | 6.17 | 5.05 | 5.37 | 5.37 | 5.53 |
| | 107 | 5.13 | 6.89 | 6.57 | 7.46 | 8.10 | 8.26 | 8.66 |
| | 108 | 5.45 | 6.33 | 5.85 | 6.09 | 6.33 | 6.57 | 6.09 |
| | 109 | 6.41 | 7.13 | 6.89 | 6.09 | 5.69 | 6.65 | 6.01 |
| | Mean | 5.57 | 6.81 | 6.37 | 6.17 | 6.37 | 6.71 | 6.57 |
| | S.E. | 0.29 | 0.17 | 0.23 | 0.49 | 0.61 | 0.59 | 0.71 |
| control | 101 | 5.37 | 6.33 | 6.97 | 6.73 | 6.89 | 6.73 | 6.65 |
| | 102 | 6.01 | 7.21 | 7.46 | 8.34 | 8.82 | 8.66 | 8.90 |
| | 103 | 6.01 | 7.54 | 7.38 | 7.70 | 8.50 | 8.26 | 9.14 |
| | 104 | 4.97 | 6.17 | 7.30 | 8.02 | 8.74 | 8.66 | 8.90 |
| | Mean | 5.59 | 6.81 | 7.28 | 7.70 | 8.24 | 8.08 | 8.40 |
| | S.E. | 0.26 | 0.33 | 0.11 | 0.35 | 0.45 | 0.46 | 0.59 |

TABLE 7

Trend of Left Ventricular Anterior Wall End-Diastolic Thickness (LVAWd = IVSTd) of the Rat Heart Failure Model by Administration of the CD106+ Rat Fibroblasts (represented as "VCF" in the table)

| Groups | Animal Number | IVSTd (mm) at each week after cell injection | | | | | | |
|---|---|---|---|---|---|---|---|---|
| | | 0 W | 2 W | 4 W | 8 W | 12 W | 16 W | 18 W |
| +VCF | 106 | 2.65 | 0.96 | 0.88 | 0.96 | 0.88 | 0.96 | 1.36 |
| | 107 | 1.36 | 1.28 | 1.28 | 0.72 | 0.96 | 0.96 | 0.96 |
| | 108 | 1.92 | 0.96 | 1.04 | 1.20 | 1.52 | 1.44 | 1.52 |
| | 109 | 2.40 | 1.52 | 1.36 | 0.88 | 0.88 | 0.96 | 0.96 |
| | Mean | 2.08 | 1.18 | 1.14 | 0.94 | 1.06 | 1.08 | 1.20 |
| | S.E. | 0.28 | 0.14 | 0.11 | 0.10 | 0.15 | 0.12 | 0.14 |
| control | 101 | 2.65 | 1.20 | 1.44 | 1.20 | 1.04 | 1.36 | 1.44 |
| | 102 | 2.40 | 1.20 | 1.04 | 0.72 | 0.80 | 0.80 | 0.88 |
| | 103 | 1.84 | 0.72 | 0.96 | 0.80 | 0.96 | 0.88 | 0.72 |
| | 104 | 2.16 | 1.12 | 1.36 | 0.96 | 1.04 | 1.20 | 1.12 |
| | Mean | 2.26 | 1.06 | 1.20 | 0.92 | 0.96 | 1.06 | 1.04 |
| | S.E. | 0.17 | 0.11 | 0.12 | 0.11 | 0.06 | 0.13 | 0.16 |

TABLE 8

Trend of Left Ventricular Posterior Wall End-Diastolic Thickness (LVPWTd) of the Rat Heart Failure Model by Administration of the CD106+ Rat Fibroblasts (represented as "VCF" in the table)

| Groups | Animal Number | LVPWTd (mm) at each week after cell injection | | | | | | |
|---|---|---|---|---|---|---|---|---|
| | | 0 W | 2 W | 4 W | 8 W | 12 W | 16 W | 18 W |
| +VCF | 106 | 1.92 | 1.76 | 1.60 | 1.12 | 1.20 | 1.20 | 1.20 |
| | 107 | 1.84 | 1.44 | 1.60 | 1.36 | 1.36 | 1.20 | 1.52 |
| | 108 | 2.16 | 1.60 | 1.36 | 1.52 | 1.52 | 1.36 | 1.76 |
| | 109 | 1.92 | 1.52 | 1.60 | 1.52 | 2.57 | 1.76 | 1.04 |
| | Mean | 1.96 | 1.58 | 1.54 | 1.38 | 1.66 | 1.38 | 1.38 |
| | S.E. | 0.07 | 0.07 | 0.06 | 0.09 | 0.31 | 0.13 | 0.16 |
| control | 101 | 1.84 | 1.44 | 1.44 | 1.36 | 1.28 | 1.36 | 1.52 |
| | 102 | 1.84 | 1.36 | 1.28 | 1.28 | 1.28 | 1.52 | 1.36 |
| | 103 | 1.36 | 1.68 | 1.36 | 0.80 | 1.04 | 1.28 | 0.96 |
| | 104 | 2.00 | 1.28 | 1.36 | 0.96 | 0.96 | 1.28 | 1.28 |
| | Mean | 1.76 | 1.44 | 1.36 | 1.10 | 1.14 | 1.36 | 1.28 |
| | S.E. | 0.14 | 0.09 | 0.03 | 0.13 | 0.08 | 0.06 | 0.12 |

TABLE 9

Trend of Heart Rate (HR) of the Rat Heart Failure Model by Administration of the CD106+ Rat Fibroblasts (represented as "VCF" in the table)

| Groups | Animal Number | HR (bpm) at each week after cell injection | | | | | | |
|---|---|---|---|---|---|---|---|---|
| | | 0 W | 2 W | 4 W | 8 W | 12 W | 16 W | 18 W |
| +VCF | 106 | 390.00 | 359.00 | 368.00 | 368.00 | 368.00 | 351.00 | 359.00 |
| | 107 | 343.00 | 351.00 | 411.00 | 368.00 | 335.00 | 343.00 | 319.00 |
| | 108 | 351.00 | 300.00 | 335.00 | 335.00 | 351.00 | 319.00 | 351.00 |
| | 109 | 380.00 | 359.00 | 335.00 | 351.00 | 306.00 | 343.00 | 313.00 |
| | Mean | 366.00 | 342.30 | 362.30 | 355.50 | 340.00 | 339.00 | 335.50 |
| | S.E. | 11.30 | 14.20 | 18.00 | 7.90 | 13.20 | 6.90 | 11.40 |
| control | 101 | 380.00 | 368.00 | 343.00 | 319.00 | 335.00 | 300.00 | 328.00 |
| | 102 | 435.00 | 368.00 | 359.00 | 359.00 | 390.00 | 335.00 | 335.00 |
| | 103 | 306.00 | 343.00 | 328.00 | 328.00 | 300.00 | 300.00 | 335.00 |
| | 104 | 400.00 | 335.00 | 380.00 | 343.00 | 351.00 | 328.00 | 343.00 |
| | Mean | 380.30 | 353.50 | 352.50 | 337.30 | 344.00 | 315.80 | 335.30 |
| | S.E. | 27.20 | 8.50 | 11.10 | 8.80 | 18.70 | 9.20 | 3.10 |

By the above experiments, the importance of VCAM-1-positive fibroblasts for effective treatment of chronic heart failure has been demonstrated, and it can be understood that administration of CD106+ fibroblasts can produce a desirable result in treatment of chronic heart failure. Since the injection of VCAM-1-positive fibroblasts enabled treatment of not only chronic heart failure, but also myocardial infarction as described above, it is thought to be effective also for treatment of other cardiac diseases.

<Localization of CD106+ Human Fibroblasts Among Human Cardiac Fibroblasts>

Figure 8:
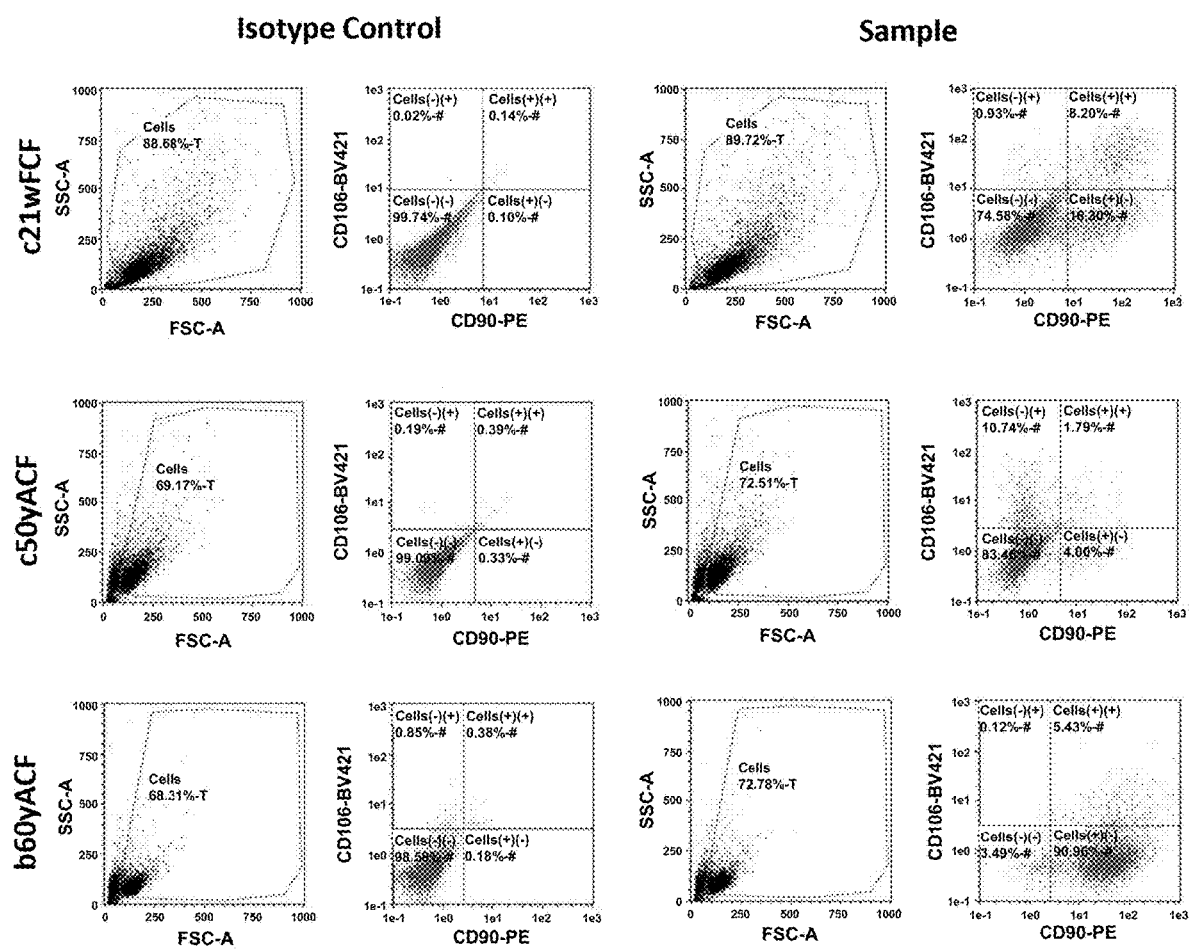
FIG. 8 shows the CD106- and CD90-positive cell ratios (%) in various cardiac fibroblasts. Caucasian fetal (21st week) heart-derived fibroblasts (c21wFCF), Caucasian adult (50's) heart-derived fibroblasts (c50yACF), and black adult (60's) heart-derived fibroblasts (b60yACF) were subjected to comparative analysis.

Cardiac fibroblasts collected from a human fetal heart (FCF) and two kinds of cardiac fibroblasts collected from human adult hearts (ACF) were provided, and evaluated by flow cytometry for the expression levels of human CD106 and human CD90, which have homologies to mouse CD106 and mouse CD90, respectively. The results are shown in FIG. 8. Two kinds of ACF were provided taking the influence of epigenetics into account. As a result, the following localization was found for c21wFCF: CD106-positive cell ratio, 9.13%; CD90-positive cell ratio, 24.5%; double-positive cell (CD106+ human fibroblast) ratio, 8.20%. The following localization was found for c50yACF: CD106-positive cell ratio, 12.53%; CD90-positive cell ratio, 5.79%; double-positive cell (CD106+ human fibroblast) ratio, 1.79%. The following localization was found for b60yACF: CD106-positive cell ratio, 5.55%; CD90-positive cell ratio, 96.39%; double-positive cell (CD106+ human fibroblast) ratio, 5.43%. All of the positive cell ratios described above are values in terms of the cell number.

It became clear, from these results, that all cardiac fibroblasts contain CD106+ human fibroblasts localized therein.

<Cell Sorting of CD106+ Human Fibroblasts>

Figure 9:
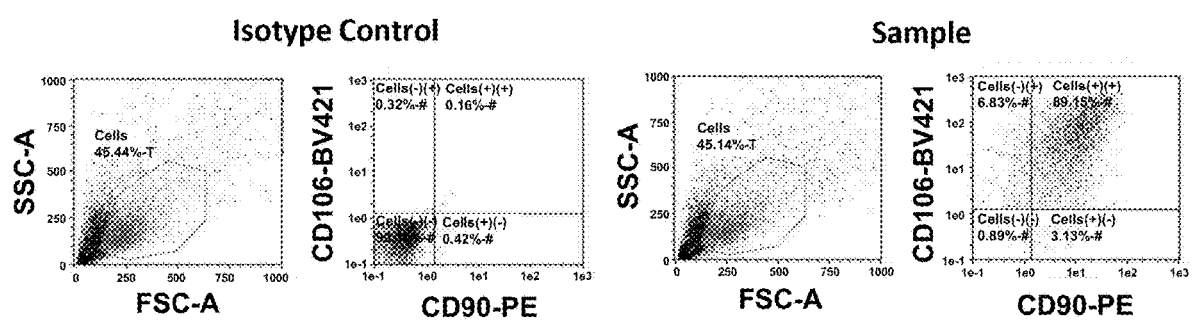
FIG. 9 shows the CD106-CD90-positive cell ratio (%) in CD106-positive human fibroblasts collected by sorting by autoMACS.

In order to collect CD106+ human fibroblasts at high purity from cardiac fibroblasts collected from a human heart, cell sorting of CD106+ human fibroblasts were carried out by autoMACS. Cell properties of the CD106+ human fibroblasts obtained by the sorting by autoMACS were evaluated. The results are shown in FIG. 9. The collected CD106+ human fibroblasts were found to contain 95.98% CD106-positive cells, 92.28% CD90-positive cells, and 89.15% double-positive cells. It was thus became clear that almost all cells are positive for CD106 and/or CD90, which are marker proteins indicating a population of CD106+ human fibroblasts. All of the positive cell ratios described above are values in terms of the cell number.

Figure 10:
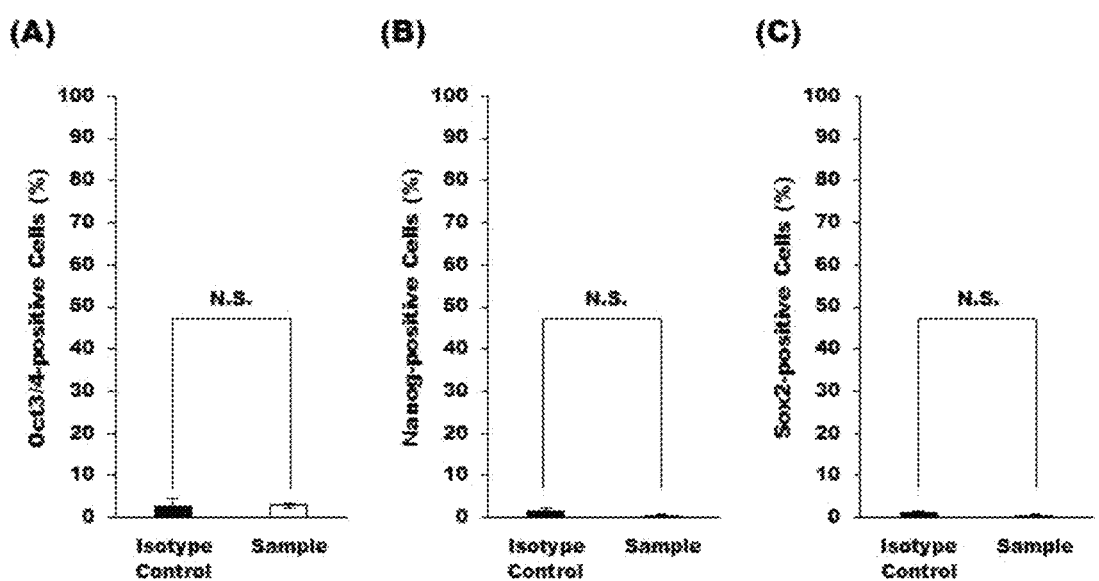
FIG. 10 shows: the Oct3/4-positive cell ratio (%) in CD106-positive human fibroblasts (A); the Nanog-positive cell ratio (%) in CD106-positive human fibroblasts (B); and the Sox2-positive cell ratio (%) in CD106-positive human fibroblasts (C). N=3. N.S.=not significant.

In order to evaluate whether the CD106+ human fibroblasts are positive for markers of tumorigenicity and pluripotent stem cells, CD106+ human fibroblasts were subjected to immunofluorescence staining with Oct3/4, Nanog, and Sox2, and the positive cell ratios (%, in terms of the cell number) were evaluated. The results are shown in FIG. 10. The CD106+ human fibroblasts were negative for the above markers, and did not have the properties of tumorigenicity or pluripotent stem cells.

<Cell Properties of CD106+ Human Fibroblasts>

Figure 11:
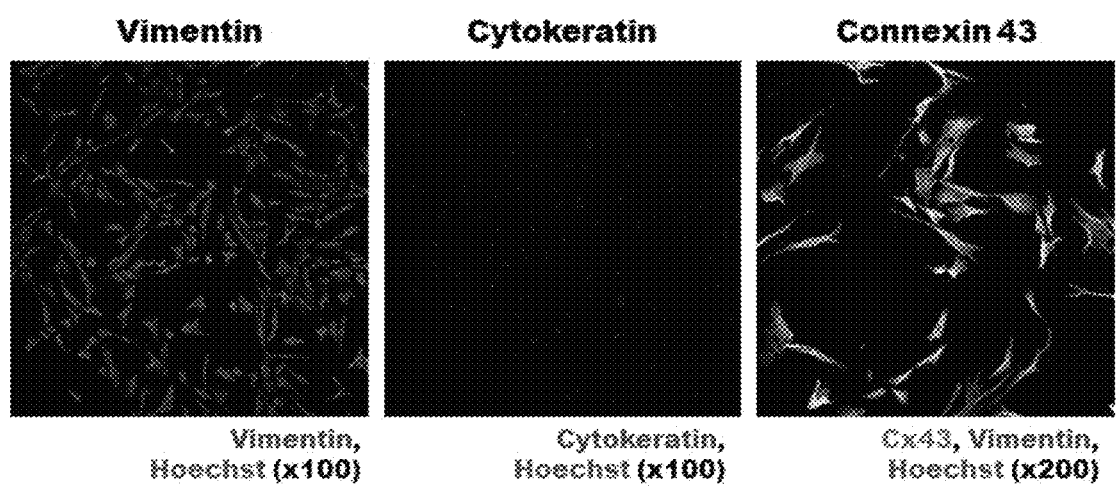
FIG. 11 shows cell properties of CD106-positive human fibroblasts. Localizations of a stromal cell/mesenchymal stem cell marker (vimentin), an epithelial cell marker (cytokeratin), and a cardiomyocyte gap junction marker (connexin 43) were evaluated.

As a result of immunofluorescence staining of the CD106+ human fibroblasts for vimentin, which is a marker of cytoskeleton of fibroblasts and mesenchymal stem cells, for cytokeratin, which is a marker of epithelial cells, and for connexin 43, which is a marker of gap junctions of cardiomyocytes, all CD106+ human fibroblasts were found to show expression of vimentin and connexin 43. The results are shown in FIG. 11.

Figure 12:
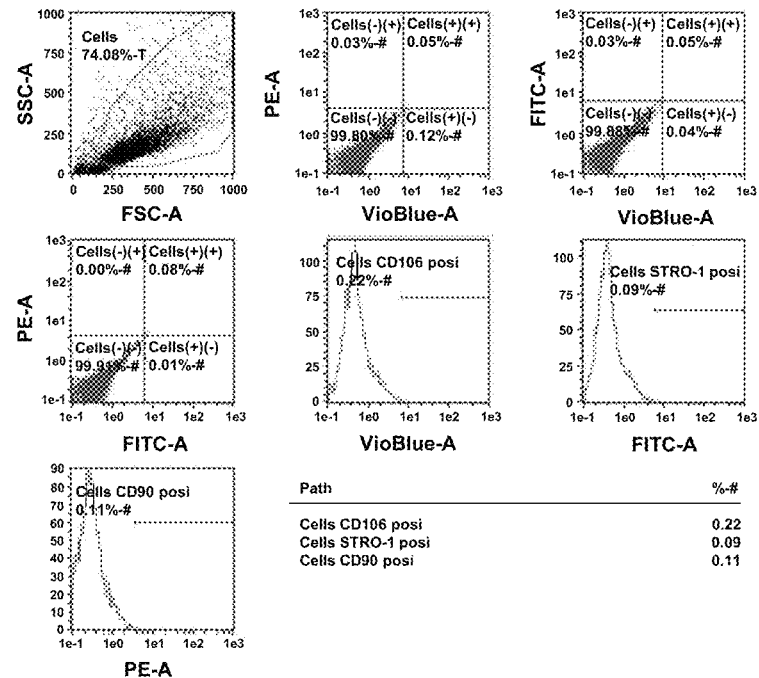
FIG. 12 shows the STRO-1-positive cell ratio (%) in CD106-positive human fibroblasts. After recognition of the cellular area with FSC-A and SSC-A, the ratio (%) of STRO-1 (FITC-A)-positive cells in a cell population that is double-positive for CD106 (VioBlue-A) and CD90 (PE-A) was evaluated. As negative controls, isotype controls for the above antibodies were used.
Figure 12:
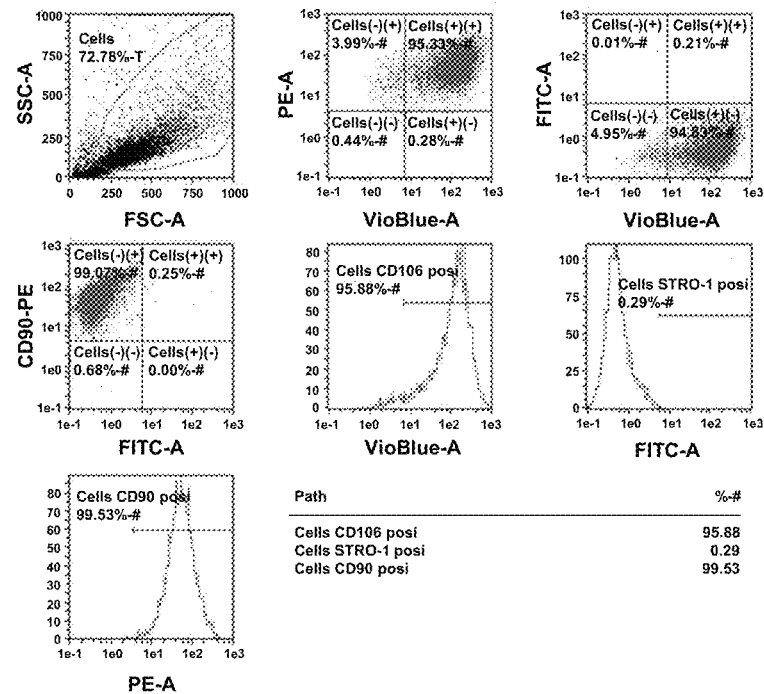

Further, as result of evaluation of the STRO-1 expression rate of the CD106+ human fibroblasts by flow cytometry, it was found that the CD106+ human fibroblasts are 0.29% positive for STRO-1, and therefore that almost none of the CD106+ human fibroblasts show expression of STRO-1. The results are shown in FIG. 12. "STRO-1, one of the best known molecular markers of mesenchymal stem cells (MSCs), is a single-pass transmembrane protein whose localization changes from the endoplasmic reticulum to the cell membrane in response to loss of intracellular calcium (Barkhordarian A, Sison J, Cayabyab R, et al. Epigenetic regulation of osteogenesis: human embryonic palatal mesenchymal cells. Bioinformation 2011; 5:278-281.). It is known that a cell population having high colony-forming ability and pluripotency can be obtained by isolation of a STRO-1-positive, glycophorin A-negative cell fraction from bone marrow stromal cells (Simmons P J, Torok-Storb B. Identification of stromal cell precursors in human bone marrow by a novel monoclonal antibody, STRO-1. Blood 1991; 78: 55-62., Tomohiko Kazama. Basic Research and Clinical Application in Mesenchymal Stem Cells. Journal of Nihon University Medical Association. 2016; 75(2): 61-66.)."

<Therapeutic Effect of CD106+ Human Fibroblasts on Rat Chronic Heart Failure Model>

Figure 13:
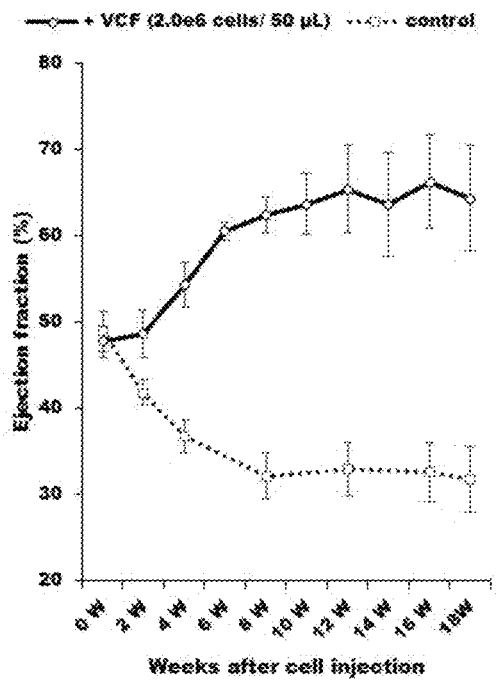
FIG. 13 shows the effect of administration of CD106-positive human fibroblasts ($2.0 \times 10^6$ cells/50 µL) on recovery of cardiac functions in a rat chronic heart failure model. (A) represents the left ventricular ejection fraction (LVEF=(LVIDd3−LVIDs3)/LVIDd3); (B) represents the left ventricular fractional shortening (LVFS=(LVIDd−LVIDs)×100/LVIDd); (C) represents the left ventricular end-diastolic volume (LVEDV); and (D) represents the left ventricular end-systolic volume (LVESV). N=4.
Figure 13:
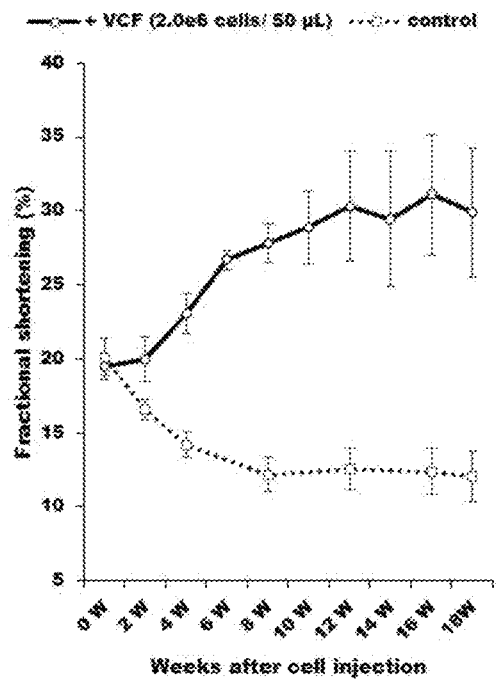
Figure 13:
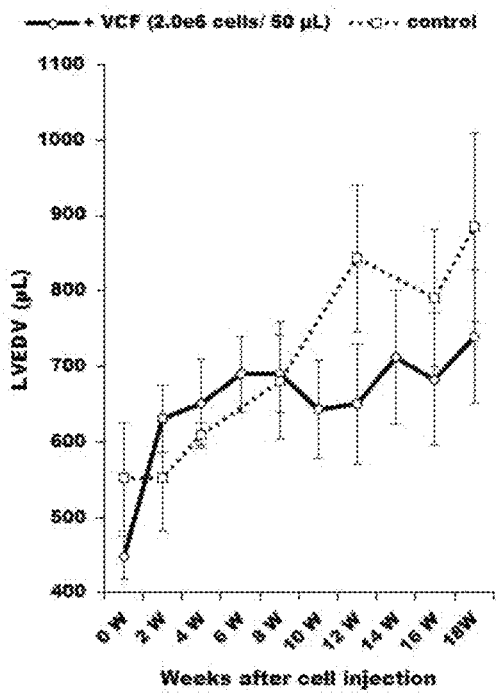
Figure 13:
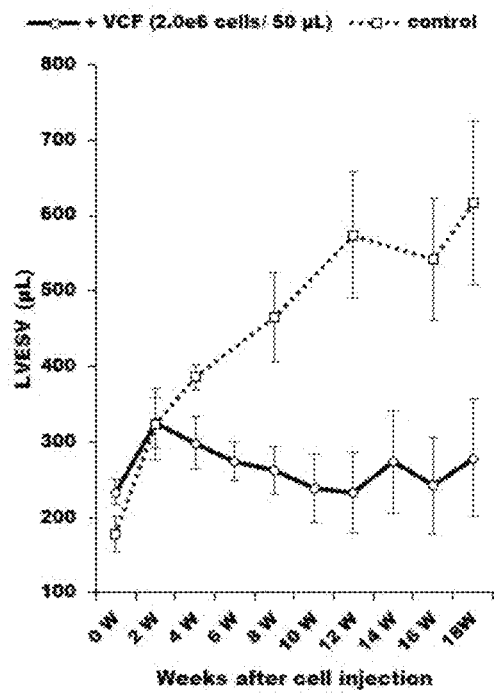

The CD106+ human fibroblasts collected after the sorting were intramyocardially administered to the rat chronic heart failure model, and the effect on recovery from heart failure was evaluated for 18 weeks after the administration of the cells. The results are shown in FIG. 13. The group in which the CD106+ human fibroblasts were administered was found to show 32.60% improvement of EF and 17.85% improvement of FS compared to the control, at Week 18 after the administration. Neither an extreme increase/decrease in LVEDV nor an increase in LVESV was found throughout the 18 weeks after the administration. The results for the main items (LVEF, LVFS, LVEDV, and LVESV) and the sub-items (LVIDd, LVIDs, IVSTd, LVPWTd, and HR) are shown in Tables 10 to 18. In terms of the results for the control, results obtained by the experiment on the therapeutic effect of the CD106+ rat fibroblasts on the rat chronic heart failure model were used.

TABLE 10

Trend of Left Ventricular Ejection Fraction (LVEF) of the Rat Heart Failure Model by Administration of the CD106+ Human Fibroblasts (represented as "VCF" in the table)

| Groups | Animal Number | LVEF (%) at each week after cell injection | | | | | | | | | |
|---|---|---|---|---|---|---|---|---|---|---|---|
| | | 0 W | 2 W | 4 W | 6 W | 8 W | 10 W | 12 W | 14 W | 16 W | 18 W |
| +VCF | 110 | 50.50 | 53.10 | 57.50 | 59.80 | 66.60 | 72.90 | 79.20 | 81.30 | 81.00 | 79.80 |
| | 111 | 48.80 | 43.30 | 56.20 | 63.70 | 64.50 | 65.70 | 58.30 | 59.10 | 64.90 | 67.40 |
| | 112 | 42.50 | 44.20 | 46.80 | 59.70 | 61.10 | 57.20 | 66.70 | 60.70 | 64.30 | 59.30 |
| | 113 | 49.00 | 53.90 | 56.80 | 58.90 | 57.20 | 59.00 | 57.30 | 53.40 | 54.80 | 50.90 |
| | Mean | 47.70 | 48.63 | 54.33 | 60.53 | 62.35 | 63.70 | 65.38 | 63.63 | 66.25 | 64.35 |
| | S.E. | 1.77 | 2.83 | 2.52 | 1.08 | 2.06 | 3.57 | 5.07 | 6.10 | 5.43 | 6.15 |
| control | 101 | 50.90 | 42.50 | 41.60 | N.D. | 39.10 | N.D. | 42.00 | N.D. | 42.60 | 43.00 |
| | 102 | 49.40 | 43.90 | 36.10 | N.D. | 33.20 | N.D. | 31.80 | N.D. | 30.60 | 28.20 |
| | 103 | 42.10 | 37.50 | 32.70 | N.D. | 27.70 | N.D. | 29.30 | N.D. | 29.90 | 29.30 |
| | 104 | 53.20 | 43.40 | 36.60 | N.D. | 28.70 | N.D. | 28.60 | N.D. | 27.10 | 26.50 |
| | Mean | 48.90 | 41.83 | 36.75 | N.D. | 32.18 | N.D. | 32.93 | N.D. | 32.55 | 31.75 |
| | S.E. | 2.40 | 1.47 | 1.83 | N.D. | 2.60 | N.D. | 3.10 | N.D. | 3.43 | 3.79 |

TABLE 11

Trend of Left Ventricular Fractional Shortening (LVFS) of the Rat Heart Failure Model by Administration of the CD106+ Human Fibroblasts (represented as "VCF" in the table)

| Groups | Animal Number | LVFS (%) at each week after cell injection | | | | | | | | | |
|---|---|---|---|---|---|---|---|---|---|---|---|
| | | 0 W | 2 W | 4 W | 6 W | 8 W | 10 W | 12 W | 14 W | 16 W | 18 W |
| +VCF | 110 | 20.90 | 22.30 | 24.80 | 26.20 | 30.60 | 35.30 | 40.80 | 42.90 | 42.60 | 41.40 |
| | 111 | 20.00 | 17.20 | 24.10 | 28.60 | 29.20 | 30.00 | 25.30 | 25.70 | 29.50 | 31.20 |
| | 112 | 16.90 | 17.70 | 19.00 | 26.20 | 27.00 | 24.60 | 30.70 | 26.80 | 29.00 | 25.90 |
| | 113 | 20.10 | 22.80 | 24.40 | 25.70 | 24.60 | 25.70 | 24.60 | 22.50 | 23.30 | 21.10 |
| | Mean | 19.48 | 20.00 | 23.08 | 26.68 | 27.85 | 28.90 | 30.35 | 29.48 | 31.10 | 29.90 |
| | S.E. | 0.88 | 1.48 | 1.37 | 0.65 | 1.31 | 2.43 | 3.74 | 4.57 | 4.08 | 4.35 |
| control | 101 | 21.10 | 16.90 | 16.40 | N.D. | 15.20 | N.D. | 16.60 | N.D. | 16.90 | 17.10 |
| | 102 | 20.30 | 17.50 | 13.90 | N.D. | 12.60 | N.D. | 12.00 | N.D. | 11.50 | 10.50 |
| | 103 | 16.60 | 14.50 | 12.40 | N.D. | 10.30 | N.D. | 10.90 | N.D. | 11.20 | 10.90 |
| | 104 | 22.50 | 17.30 | 14.10 | N.D. | 10.70 | N.D. | 10.60 | N.D. | 10.00 | 9.70 |
| | Mean | 20.13 | 16.55 | 14.20 | N.D. | 12.20 | N.D. | 12.53 | N.D. | 12.40 | 12.05 |
| | S.E. | 1.26 | 0.69 | 0.83 | N.D. | 1.12 | N.D. | 1.39 | N.D. | 1.53 | 1.70 |

TABLE 12

Trend of Left Ventricular End-Diastolic Volume (LVEDV) of the Rat Heart Failure Model by Administration of the CD106+ Human Fibroblasts (represented as "VCF" in the table)

| Groups | Animal Number | LVEDV (µL) at each week after cell injection | | | | | | | | | |
|---|---|---|---|---|---|---|---|---|---|---|---|
| | | 0 W | 2 W | 4 W | 6 W | 8 W | 10 W | 12 W | 14 W | 16 W | 18 W |
| +VCF | 110 | 457.00 | 501.00 | 597.00 | 632.00 | 649.00 | 547.00 | 486.00 | 486.00 | 531.00 | 580.00 |
| | 111 | 375.00 | 686.00 | 516.00 | 597.00 | 564.00 | 516.00 | 564.00 | 668.00 | 547.00 | 614.00 |
| | 112 | 442.00 | 649.00 | 705.00 | 705.00 | 784.00 | 764.00 | 705.00 | 804.00 | 764.00 | 804.00 |
| | 113 | 516.00 | 686.00 | 784.00 | 825.00 | 764.00 | 744.00 | 847.00 | 890.00 | 890.00 | 959.00 |
| | Mean | 447.50 | 630.50 | 650.50 | 689.75 | 690.25 | 642.75 | 650.50 | 712.00 | 683.00 | 739.25 |
| | S.E. | 28.97 | 44.04 | 58.98 | 50.38 | 51.53 | 64.67 | 79.65 | 88.11 | 87.09 | 88.28 |
| control | 101 | 442.00 | 442.00 | 580.00 | N.D. | 501.00 | N.D. | 564.00 | N.D. | 531.00 | 516.00 |
| | 102 | 668.00 | 668.00 | 649.00 | N.D. | 868.00 | N.D. | 1006.00 | N.D. | 935.00 | 982.00 |

TABLE 12-continued

Trend of Left Ventricular End-Diastolic Volume (LVEDV) of the Rat
Heart Failure Model by Administration of the CD106+ Human Fibroblasts (represented as
"VCF" in the table)

| Groups | Animal Number | LVEDV (µL) at each week after cell injection | | | | | | | | | |
|---|---|---|---|---|---|---|---|---|---|---|---|
| | | 0 W | 2 W | 4 W | 6 W | 8 W | 10 W | 12 W | 14 W | 16 W | 18 W |
| | 103 | 686.00 | 686.00 | 597.00 | N.D. | 632.00 | N.D. | 868.00 | N.D. | 804.00 | 1080.00 |
| | 104 | 415.00 | 415.00 | 614.00 | N.D. | 724.00 | N.D. | 935.00 | N.D. | 890.00 | 959.00 |
| | Mean | 552.75 | 552.75 | 610.00 | N.D. | 681.25 | N.D. | 843.25 | N.D. | 790.00 | 884.25 |
| | S.E. | 72.04 | 72.04 | 14.74 | N.D. | 77.25 | N.D. | 97.25 | N.D. | 90.51 | 125.52 |

TABLE 13

Trend of Left Ventricular End-Systolic Volume (LVESV) of the Rat
Heart Failure Model by Administration of the CD106+ Human Fibroblasts (represented as
"VCF" in the table)

| Groups | Animal Number | LVESV (µL) at each week after cell injection | | | | | | | | | |
|---|---|---|---|---|---|---|---|---|---|---|---|
| | | 0 W | 2 W | 4 W | 6 W | 8 W | 10 W | 12 W | 14 W | 16 W | 18 W |
| +VCF | 110 | 226.00 | 235.00 | 254.00 | 254.00 | 217.00 | 148.00 | 101.00 | 91.00 | 101.00 | 117.00 |
| | 111 | 192.00 | 389.00 | 226.00 | 217.00 | 200.00 | 177.00 | 235.00 | 273.00 | 192.00 | 200.00 |
| | 112 | 254.00 | 362.00 | 375.00 | 284.00 | 305.00 | 327.00 | 235.00 | 316.00 | 273.00 | 327.00 |
| | 113 | 263.00 | 316.00 | 339.00 | 339.00 | 327.00 | 305.00 | 362.00 | 415.00 | 402.00 | 471.00 |
| | Mean | 233.75 | 325.50 | 298.50 | 273.50 | 262.25 | 239.25 | 233.25 | 273.75 | 242.00 | 278.75 |
| | S.E. | 15.99 | 33.72 | 35.03 | 25.78 | 31.55 | 44.93 | 53.29 | 67.78 | 63.86 | 77.27 |
| control | 101 | 155.00 | 254.00 | 339.00 | N.D. | 305.00 | N.D. | 327.00 | N.D. | 305.00 | 294.00 |
| | 102 | 217.00 | 375.00 | 415.00 | N.D. | 580.00 | N.D. | 686.00 | N.D. | 649.00 | 705.00 |
| | 103 | 217.00 | 429.00 | 402.00 | N.D. | 457.00 | N.D. | 614.00 | N.D. | 564.00 | 764.00 |
| | 104 | 123.00 | 235.00 | 389.00 | N.D. | 516.00 | N.D. | 668.00 | N.D. | 649.00 | 705.00 |
| | Mean | 178.00 | 323.25 | 386.25 | N.D. | 464.50 | N.D. | 573.75 | N.D. | 541.75 | 617.00 |
| | S.E. | 23.44 | 46.94 | 16.62 | N.D. | 58.80 | N.D. | 83.66 | N.D. | 81.42 | 108.56 |

TABLE 14

Trend of Left Ventricular End-Diastolic Diameter (LVIDd) of the Rat
Heart Failure Model by Administration of the CD106+ Human
Fibroblasts (represented as "VCF" in the table)

| Groups | Animal Number | LVIDd (mm) at each week after cell injection | | | | | | | | | |
|---|---|---|---|---|---|---|---|---|---|---|---|
| | | 0 W | 2 W | 4 W | 6 W | 8 W | 10 W | 12 W | 14 W | 16 W | 18 W |
| +VCF | 110 | 7.70 | 7.94 | 8.42 | 8.58 | 8.66 | 8.18 | 7.86 | 7.86 | 8.10 | 8.34 |
| | 111 | 7.21 | 8.82 | 8.02 | 8.42 | 8.26 | 8.02 | 8.26 | 8.74 | 8.18 | 7.62 |
| | 112 | 7.62 | 8.66 | 8.90 | 8.90 | 9.22 | 9.14 | 8.90 | 9.30 | 9.14 | 8.98 |
| | 113 | 8.02 | 8.82 | 9.22 | 9.38 | 9.14 | 9.06 | 9.46 | 9.62 | 9.62 | 9.62 |
| | Mean | 7.64 | 8.56 | 8.64 | 8.82 | 8.82 | 8.60 | 8.62 | 8.88 | 8.76 | 8.64 |
| | S.E. | 0.17 | 0.21 | 0.26 | 0.21 | 0.22 | 0.29 | 0.35 | 0.39 | 0.37 | 0.43 |
| control | 101 | 6.81 | 7.62 | 8.34 | N.D. | 7.94 | N.D. | 8.26 | N.D. | 8.10 | 8.02 |
| | 102 | 7.54 | 8.74 | 8.66 | N.D. | 9.54 | N.D. | 10.02 | N.D. | 9.78 | 9.94 |
| | 103 | 7.21 | 8.82 | 8.42 | N.D. | 8.58 | N.D. | 9.54 | N.D. | 9.30 | 10.26 |
| | 104 | 6.41 | 7.46 | 8.50 | N.D. | 8.98 | N.D. | 9.78 | N.D. | 9.62 | 9.86 |
| | Mean | 6.99 | 8.16 | 8.48 | N.D. | 8.76 | N.D. | 9.40 | N.D. | 9.20 | 9.52 |
| | S.E. | 0.24 | 0.36 | 0.07 | N.D. | 0.34 | N.D. | 0.39 | N.D. | 0.38 | 0.51 |

TABLE 15

Trend of Left Ventricular End-Systolic Diameter (LVIDs) of the Rat Heart Failure Model by Administration of the CD106+ Human Fibroblasts (represented as "VCF" in the table)

| Groups | Animal Number | LVIDs (mm) at each week after cell injection | | | | | | | | | |
|---|---|---|---|---|---|---|---|---|---|---|---|
| | | 0 W | 2 W | 4 W | 6 W | 8 W | 10 W | 12 W | 14 W | 16 W | 18 W |
| +VCF | 110 | 6.09 | 6.17 | 6.33 | 6.33 | 6.01 | 5.29 | 4.65 | 4.49 | 4.65 | 4.89 |
| | 111 | 5.77 | 7.30 | 6.09 | 6.01 | 5.85 | 5.61 | 6.17 | 6.49 | 5.77 | 5.85 |
| | 112 | 6.33 | 7.13 | 7.21 | 6.57 | 6.73 | 6.89 | 6.17 | 6.81 | 6.49 | 6.89 |
| | 113 | 6.41 | 6.81 | 6.97 | 6.97 | 6.89 | 6.73 | 7.13 | 7.46 | 7.38 | 7.78 |
| | Mean | 6.15 | 6.85 | 6.65 | 6.47 | 6.37 | 6.13 | 6.03 | 6.31 | 6.07 | 6.35 |
| | S.E. | 0.14 | 0.25 | 0.26 | 0.20 | 0.26 | 0.40 | 0.51 | 0.64 | 0.58 | 0.63 |
| control | 101 | 5.37 | 6.33 | 6.97 | N.D. | 6.73 | N.D. | 6.89 | N.D. | 6.73 | 6.65 |
| | 102 | 6.01 | 7.21 | 7.46 | N.D. | 8.34 | N.D. | 8.82 | N.D. | 8.66 | 8.90 |
| | 103 | 6.01 | 7.54 | 7.38 | N.D. | 7.70 | N.D. | 8.50 | N.D. | 8.26 | 9.14 |
| | 104 | 4.97 | 6.17 | 7.30 | N.D. | 8.02 | N.D. | 8.74 | N.D. | 8.66 | 8.90 |
| | Mean | 5.59 | 6.81 | 7.28 | N.D. | 7.70 | N.D. | 8.24 | N.D. | 8.08 | 8.40 |
| | S.E. | 0.26 | 0.33 | 0.11 | N.D. | 0.35 | N.D. | 0.45 | N.D. | 0.46 | 0.59 |

TABLE 16

Trend of Left Ventricular Anterior Wall End-Diastolic Thickness (LVAWd = IVSTd) of the Rat Heart Failure Model by Administration of the CD106+ Human Fibroblasts (represented as "VCF" in the table)

| Groups | Animal Number | IVSTd (mm) at each week after cell injection | | | | | | | | | |
|---|---|---|---|---|---|---|---|---|---|---|---|
| | | 0 W | 2 W | 4 W | 6 W | 8 W | 10 W | 12 W | 14 W | 16 W | 18 W |
| +VCF | 110 | 1.36 | 1.52 | 1.92 | 1.44 | 1.76 | 2.24 | 2.40 | 2.65 | 2.49 | 2.65 |
| | 111 | 1.76 | 1.20 | 1.92 | 1.44 | 1.52 | 1.52 | 2.16 | 1.76 | 2.24 | 2.16 |
| | 112 | 1.36 | 1.04 | 0.80 | 1.04 | 1.20 | 1.36 | 1.76 | 1.60 | 1.04 | 1.28 |
| | 113 | 1.20 | 1.52 | 1.28 | 1.20 | 1.36 | 1.44 | 1.04 | 1.04 | 1.12 | 0.96 |
| | Mean | 1.42 | 1.32 | 1.48 | 1.28 | 1.46 | 1.64 | 1.84 | 1.76 | 1.72 | 1.76 |
| | S.E. | 0.12 | 0.12 | 0.27 | 0.10 | 0.12 | 0.20 | 0.30 | 0.33 | 0.37 | 0.39 |
| control | 101 | 2.65 | 1.20 | 1.44 | N.D. | 1.20 | N.D. | 1.04 | N.D. | 1.36 | 1.44 |
| | 102 | 2.40 | 1.20 | 1.04 | N.D. | 0.72 | N.D. | 0.80 | N.D. | 0.80 | 0.88 |
| | 103 | 1.84 | 0.72 | 0.96 | N.D. | 0.80 | N.D. | 0.96 | N.D. | 0.88 | 0.72 |
| | 104 | 2.16 | 1.12 | 1.36 | N.D. | 0.96 | N.D. | 1.04 | N.D. | 1.20 | 1.12 |
| | Mean | 2.26 | 1.06 | 1.20 | N.D. | 0.92 | N.D. | 0.96 | N.D. | 1.06 | 1.04 |
| | S.E. | 0.17 | 0.11 | 0.12 | N.D. | 0.11 | N.D. | 0.06 | N.D. | 0.13 | 0.16 |

TABLE 17

Trend of Left Ventricular Posterior Wall End-Diastolic Thickness (LVPWTd) of the Rat Heart Failure Model by Administration of the CD106+ Human Fibroblasts (represented as "VCF" in the table)

| Groups | Animal Number | LVPWTd (mm) at each week after cell injection | | | | | | | | | |
|---|---|---|---|---|---|---|---|---|---|---|---|
| | | 0 W | 2 W | 4 W | 6 W | 8 W | 10 W | 12 W | 14 W | 16 W | 18 W |
| +VCF | 110 | 1.36 | 1.20 | 2.08 | 2.08 | 1.68 | 2.32 | 2.08 | 2.65 | 1.68 | 1.76 |
| | 111 | 1.20 | 1.68 | 1.76 | 1.84 | 1.84 | 1.52 | 1.76 | 1.76 | 1.44 | 1.60 |
| | 112 | 1.36 | 1.44 | 1.68 | 1.68 | 1.68 | 1.84 | 1.68 | 1.60 | 1.84 | 1.68 |
| | 113 | 2.00 | 1.84 | 1.76 | 1.76 | 2.08 | 1.68 | 1.68 | 1.04 | 1.68 | 1.60 |
| | Mean | 1.48 | 1.54 | 1.82 | 1.84 | 1.82 | 1.84 | 1.80 | 1.76 | 1.66 | 1.66 |
| | S.E. | 0.18 | 0.14 | 0.09 | 0.09 | 0.09 | 0.17 | 0.10 | 0.33 | 0.08 | 0.04 |
| control | 101 | 1.28 | 1.36 | 1.20 | 2.08 | 2.08 | N.D. | 2.32 | N.D. | 1.36 | 1.52 |
| | 102 | 1.52 | 1.20 | 1.68 | 1.76 | 1.84 | N.D. | 1.52 | N.D. | 1.52 | 1.36 |
| | 103 | 1.28 | 1.36 | 1.44 | 1.68 | 1.68 | N.D. | 1.84 | N.D. | 1.28 | 0.96 |
| | 104 | 2.32 | 2.00 | 1.84 | 1.76 | 1.76 | N.D. | 1.68 | N.D. | 1.28 | 1.28 |
| | Mean | 1.60 | 1.48 | 1.54 | 1.82 | 1.84 | N.D. | 1.84 | N.D. | 1.36 | 1.28 |
| | S.E. | 0.25 | 0.18 | 0.14 | 0.09 | 0.09 | N.D. | 0.17 | N.D. | 0.06 | 0.12 |

TABLE 18

Trend of Heart Rate (HR) of the Rat Heart Failure Model by Administration of the CD106+ Human Fibroblasts (represented as "VCF" in the table)

| Groups | Animal Number | HR (bpm) at each week after cell injection | | | | | | | | | |
|---|---|---|---|---|---|---|---|---|---|---|---|
| | | 0 W | 2 W | 4 W | 6 W | 8 W | 10 W | 12 W | 14 W | 16 W | 18 W |
| +VCF | 110 | 335.00 | 359.00 | 368.00 | 313.00 | 306.00 | 328.00 | 319.00 | 335.00 | 313.00 | 343.00 |
| | 111 | 359.00 | 343.00 | 319.00 | 313.00 | 319.00 | 319.00 | 328.00 | 306.00 | 294.00 | 319.00 |
| | 112 | 359.00 | 300.00 | 359.00 | 359.00 | 343.00 | 328.00 | 343.00 | 335.00 | 351.00 | 359.00 |
| | 113 | 343.00 | 335.00 | 368.00 | 319.00 | 380.00 | 328.00 | 328.00 | 335.00 | 319.00 | 343.00 |
| | Mean | 349.00 | 334.25 | 353.50 | 326.00 | 337.00 | 325.75 | 329.50 | 327.75 | 319.25 | 341.00 |
| | S.E. | 6.00 | 12.46 | 11.69 | 11.09 | 16.25 | 2.25 | 4.97 | 7.25 | 11.85 | 8.25 |
| control | 101 | 380.00 | 368.00 | 343.00 | 2.08 | 319.00 | N.D. | 335.00 | N.D. | 300.00 | 328.00 |
| | 102 | 435.00 | 368.00 | 359.00 | 1.76 | 359.00 | N.D. | 390.00 | N.D. | 335.00 | 335.00 |
| | 103 | 306.00 | 343.00 | 328.00 | 1.68 | 328.00 | N.D. | 300.00 | N.D. | 300.00 | 335.00 |
| | 104 | 400.00 | 335.00 | 380.00 | 1.76 | 343.00 | N.D. | 351.00 | N.D. | 328.00 | 343.00 |
| | Mean | 380.25 | 353.50 | 352.50 | 1.82 | 337.25 | N.D. | 344.00 | N.D. | 315.75 | 335.25 |
| | S.E. | 27.23 | 8.53 | 11.14 | 0.09 | 8.78 | N.D. | 18.67 | N.D. | 9.20 | 3.07 |

<Study of Dose of CD106+ Human Fibroblasts>

Figure 14:
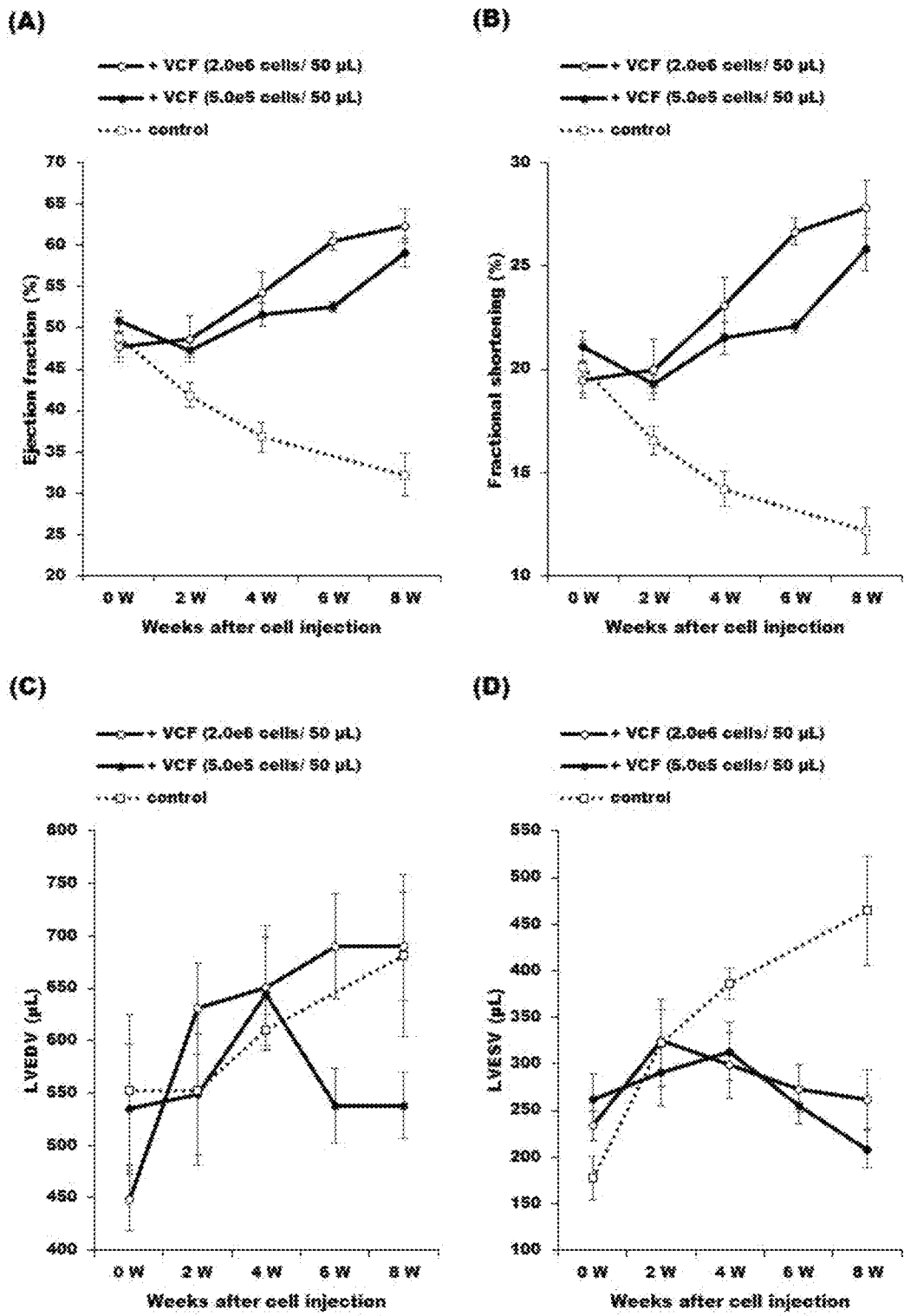
FIG. 14 shows the effects of administration of CD106-positive human fibroblasts at different doses on recovery of cardiac functions in a rat chronic heart failure model. (A) represents the left ventricular ejection fraction (LVEF=(LVIDd3−LVIDs3)/LVIDd3); (B) represents the left ventricular fractional shortening (LVFS=(LVIDd−LVIDs)×100/LVIDd); (C) represents the left ventricular end-diastolic volume (LVEDV); and (D) represents the left ventricular end-systolic volume (LVESV). N=4. N.S.=not significant.

The CD106+ human fibroblasts collected after the sorting were intramyocardially administered at two kinds of concentrations ($2.0 \times 10^6$ cells/50 µL and $5.0 \times 10^5$ cells/50 µL) to the rat chronic heart failure model, and the effect on recovery from heart failure was evaluated for 8 weeks after the administration of the cells. The results are shown in FIG. 14. The group in which the CD106+ human fibroblasts ($2.0 \times 10^6$ cells/50 µL) were administered was found to show 30.18% improvement of EF and 15.65% improvement of FS compared to the control, at Week 8 after the administration. Neither an extreme increase/decrease in LVEDV nor an increase in LVESV was found throughout the 8 weeks after the administration. The group in which the CD106+ human fibroblasts ($5.0 \times 10^5$ cells/50 µL) were administered was found to show 26.90% improvement of EF and 13.63% improvement of FS compared to the control, at Week 8 after the administration. At Week 8 after the administration, no significant difference in EF or FS was found between the group in which the CD106+ human fibroblasts ($2.0 \times 10^6$ cells/50 µL) were administered and the group in which the CD106+ human fibroblasts ($5.0 \times 10^5$ cells/50 µL) were administered. However, it became clear that, as the dose increases, the therapeutic effect on heart failure can be found earlier. In terms of the results for the control, results obtained by the experiment on the therapeutic effect of the CD106+ rat fibroblasts on the rat chronic heart failure model were used. In terms of the results for the group in which the CD106+ human fibroblasts ($2.0 \times 10^6$ cells/50 µL) were administered, the results obtained in Table 2 were used.

The results for the main items (LVEF, LVFS, LVEDV, and LVESV) and the results for the sub-items (LVIDd, LVIDs, IVSTd, LVPWTd, and HR) are shown in Tables 19 to 27.

TABLE 19

Trend of Left Ventricular Ejection Fraction (LVEF) of the Rat Heart Failure Model due to the difference in dosage of the CD106+ Human Fibroblasts (represented as "VCF" in the table)

| Groups | Animal Number | LVEF (%) at each week after cell injection | | | | |
|---|---|---|---|---|---|---|
| | | 0 W | 2 W | 4 W | 6 W | 8 W |
| +VCF (2.0e6 cells/50 µL) | 110 | 50.50 | 53.10 | 57.50 | 59.80 | 66.60 |
| | 111 | 48.80 | 43.30 | 56.20 | 63.70 | 64.50 |
| | 112 | 42.50 | 44.20 | 46.80 | 59.70 | 61.10 |
| | 113 | 49.00 | 53.90 | 56.80 | 58.90 | 57.20 |
| | Mean | 47.70 | 48.63 | 54.33 | 60.53 | 62.35 |
| | S.E. | 1.77 | 2.83 | 2.52 | 1.08 | 2.06 |
| +VCF (5.0e5 cells/50 µL) | 201 | 50.90 | 47.70 | 49.30 | 52.20 | 55.40 |
| | 202 | 51.30 | 47.90 | 50.40 | 52.20 | 62.70 |
| | 203 | 47.50 | 44.80 | 50.90 | 51.70 | 57.00 |
| | 204 | 53.70 | 48.90 | 55.70 | 54.30 | 61.20 |
| | Mean | 50.85 | 47.33 | 51.58 | 52.60 | 59.08 |
| | S.E. | 1.28 | 0.88 | 1.42 | 0.58 | 1.72 |
| control | 101 | 50.90 | 42.50 | 41.60 | N.D. | 39.10 |
| | 102 | 49.40 | 43.90 | 36.10 | N.D. | 33.20 |
| | 103 | 42.10 | 37.50 | 32.70 | N.D. | 27.70 |
| | 104 | 53.20 | 43.40 | 36.60 | N.D. | 28.70 |
| | Mean | 48.90 | 41.83 | 36.75 | N.D. | 32.18 |
| | S.E. | 2.40 | 1.47 | 1.83 | N.D. | 2.60 |

TABLE 20

Trend of Left Ventricular Fractional Shortening (LVFS) of the Rat Heart Failure Model due to the difference in dosage of the CD106+ Human Fibroblasts (represented as "VCF" in the table)

| Groups | Animal Number | LVFS (%) at each week after cell injection | | | | |
|---|---|---|---|---|---|---|
| | | 0 W | 2 W | 4 W | 6 W | 8 W |
| +VCF (2.0e6 cells/50 µL) | 110 | 20.90 | 22.30 | 24.80 | 26.20 | 30.60 |
| | 111 | 20.00 | 17.20 | 24.10 | 28.60 | 29.20 |
| | 112 | 16.90 | 17.70 | 19.00 | 26.20 | 27.00 |
| | 113 | 20.10 | 22.80 | 24.40 | 25.70 | 24.60 |
| | Mean | 19.48 | 20.00 | 23.08 | 26.68 | 27.85 |
| | S.E. | 0.88 | 1.48 | 1.37 | 0.65 | 1.31 |
| +VCF (5.0e5 cells/50 µL) | 201 | 21.10 | 19.50 | 20.30 | 21.90 | 23.60 |
| | 202 | 21.40 | 19.50 | 20.80 | 21.90 | 28.00 |
| | 203 | 19.30 | 18.00 | 21.10 | 21.60 | 24.60 |
| | 204 | 22.70 | 20.10 | 23.80 | 23.00 | 27.10 |
| | Mean | 21.13 | 19.28 | 21.50 | 22.10 | 25.83 |
| | S.E. | 0.70 | 0.45 | 0.78 | 0.31 | 1.03 |
| control | 101 | 21.10 | 16.90 | 16.40 | N.D. | 15.20 |
| | 102 | 20.30 | 17.50 | 13.90 | N.D. | 12.60 |
| | 103 | 16.60 | 14.50 | 12.40 | N.D. | 10.30 |
| | 104 | 22.50 | 17.30 | 14.10 | N.D. | 10.70 |
| | Mean | 20.13 | 16.55 | 14.20 | N.D. | 12.20 |
| | S.E. | 1.26 | 0.69 | 0.83 | N.D. | 1.12 |

TABLE 21

Trend of Left Ventricular End-Diastolic Volume (LVEDV) of the Rat Heart Failure Model due to the difference in dosage of the CD106+ Human Fibroblasts (represented as "VCF" in the table)

| Groups | Animal Number | LVEDV (µL) at each week after cell injection | | | | |
|---|---|---|---|---|---|---|
| | | 0 W | 2 W | 4 W | 6 W | 8 W |
| +VCF (2.0e6 cells/ 50 µL) | 110 | 457.00 | 501.00 | 597.00 | 632.00 | 649.00 |
| | 111 | 375.00 | 686.00 | 516.00 | 597.00 | 564.00 |
| | 112 | 442.00 | 649.00 | 705.00 | 705.00 | 784.00 |
| | 113 | 516.00 | 686.00 | 784.00 | 825.00 | 764.00 |
| | Mean | 447.50 | 630.50 | 650.50 | 689.75 | 690.25 |
| | S.E. | 28.97 | 44.04 | 58.98 | 50.38 | 51.53 |
| +VCF (5.0e5 cells/ 50 µL) | 201 | 375.00 | 486.00 | 580.00 | 531.00 | 547.00 |
| | 202 | 649.00 | 564.00 | 705.00 | 531.00 | 415.00 |
| | 203 | 501.00 | 705.00 | 764.00 | 632.00 | 547.00 |
| | 204 | 614.00 | 442.00 | 531.00 | 457.00 | 516.00 |
| | Mean | 534.75 | 549.25 | 645.00 | 537.75 | 506.25 |
| | S.E. | 61.91 | 57.72 | 53.99 | 35.93 | 31.28 |
| control | 101 | 442.00 | 442.00 | 580.00 | N.D. | 501.00 |
| | 102 | 668.00 | 668.00 | 649.00 | N.D. | 868.00 |
| | 103 | 686.00 | 686.00 | 597.00 | N.D. | 632.00 |
| | 104 | 415.00 | 415.00 | 614.00 | N.D. | 724.00 |
| | Mean | 552.75 | 552.75 | 610.00 | N.D. | 681.25 |
| | S.E. | 72.04 | 72.04 | 14.74 | N.D. | 77.25 |

TABLE 22

Trend of Left Ventricular End-Systolic Volume (LVESV) of the Rat Heart Failure Model due to the difference in dosage of the CD106+ Human Fibroblasts (represented as "VCF" in the table)

| Groups | Animal Number | LVESV (µL) at each week after cell injection | | | | |
|---|---|---|---|---|---|---|
| | | 0 W | 2 W | 4 W | 6 W | 8 W |
| +VCF (2.0e6 cells/ 50 µL) | 110 | 226.00 | 235.00 | 254.00 | 254.00 | 217.00 |
| | 111 | 192.00 | 389.00 | 226.00 | 217.00 | 200.00 |
| | 112 | 254.00 | 362.00 | 375.00 | 284.00 | 305.00 |
| | 113 | 263.00 | 316.00 | 339.00 | 339.00 | 327.00 |
| | Mean | 233.75 | 325.50 | 298.50 | 273.50 | 262.25 |
| | S.E. | 15.99 | 33.72 | 35.03 | 25.78 | 31.55 |
| +VCF (5.0e5 cells/ 50 µL) | 201 | 184.00 | 254.00 | 294.00 | 254.00 | 244.00 |
| | 202 | 316.00 | 294.00 | 350.00 | 254.00 | 155.00 |
| | 203 | 263.00 | 389.00 | 375.00 | 305.00 | 235.00 |
| | 204 | 284.00 | 226.00 | 235.00 | 209.00 | 200.00 |
| | Mean | 261.75 | 290.75 | 313.50 | 255.50 | 208.50 |
| | S.E. | 28.11 | 35.60 | 31.17 | 19.62 | 20.20 |
| control | 101 | 155.00 | 254.00 | 339.00 | N.D. | 305.00 |
| | 102 | 217.00 | 375.00 | 415.00 | N.D. | 580.00 |
| | 103 | 217.00 | 429.00 | 402.00 | N.D. | 457.00 |
| | 104 | 123.00 | 235.00 | 389.00 | N.D. | 516.00 |
| | Mean | 178.00 | 323.25 | 386.25 | N.D. | 464.50 |
| | S.E. | 23.44 | 46.94 | 16.62 | N.D. | 58.80 |

TABLE 23

Trend of Left Ventricular End-Diastolic Diameter (LVIDd) of the Rat Heart Failure Model due to the difference in dosage of the CD106+ Human Fibroblasts (represented as "VCF" in the table)

| Groups | Animal Number | LVIDd (mm) at each week after cell injection | | | | |
|---|---|---|---|---|---|---|
| | | 0 W | 2 W | 4 W | 6 W | 8 W |
| +VCF (2.0e6 cells/50 µL) | 110 | 7.70 | 7.94 | 8.42 | 8.58 | 8.66 |
| | 111 | 7.21 | 8.82 | 8.02 | 8.42 | 8.26 |
| | 112 | 7.62 | 8.66 | 8.90 | 8.90 | 9.22 |
| | 113 | 8.02 | 8.82 | 9.22 | 9.38 | 9.14 |
| | Mean | 7.64 | 8.56 | 8.64 | 8.82 | 8.82 |
| | S.E. | 0.17 | 0.21 | 0.26 | 0.21 | 0.22 |
| +VCF (5.0e5 cells/50 µL) | 201 | 7.21 | 7.86 | 8.34 | 8.10 | 8.18 |
| | 202 | 8.66 | 8.26 | 8.90 | 8.10 | 7.46 |
| | 203 | 7.94 | 8.90 | 9.14 | 8.58 | 8.18 |
| | 204 | 8.50 | 7.62 | 8.10 | 7.70 | 8.02 |
| | Mean | 8.08 | 8.16 | 8.62 | 8.12 | 7.96 |
| | S.E. | 0.33 | 0.28 | 0.24 | 0.18 | 0.17 |
| control | 101 | 6.81 | 7.62 | 8.34 | N.D. | 7.94 |
| | 102 | 7.54 | 8.74 | 8.66 | N.D. | 9.54 |
| | 103 | 7.21 | 8.82 | 8.42 | N.D. | 8.58 |
| | 104 | 6.41 | 7.46 | 8.50 | N.D. | 8.98 |
| | Mean | 6.99 | 8.16 | 8.48 | N.D. | 8.76 |
| | S.E. | 0.24 | 0.36 | 0.07 | N.D. | 0.34 |

TABLE 24

Trend of Left Ventricular End-Systolic Diameter (LVIDs) of the Rat Heart Failure Model due to the difference in dosage of the CD106+ Human Fibroblasts (represented as "VCF" in the table)

| Groups | Animal Number | LVIDs (mm) at each week after cell injection | | | | |
|---|---|---|---|---|---|---|
| | | 0 W | 2 W | 4 W | 6 W | 8 W |
| +VCF (2.0e6 cells/50 µL) | 110 | 6.09 | 6.17 | 6.33 | 6.33 | 6.01 |
| | 111 | 5.77 | 7.30 | 6.09 | 6.01 | 5.85 |
| | 112 | 6.33 | 7.13 | 7.21 | 6.57 | 6.73 |
| | 113 | 6.41 | 6.81 | 6.97 | 6.97 | 6.89 |
| | Mean | 6.15 | 6.85 | 6.65 | 6.47 | 6.37 |
| | S.E. | 0.14 | 0.25 | 0.26 | 0.20 | 0.26 |
| +VCF (5.0e5 cells/50 µL) | 201 | 5.69 | 6.33 | 6.65 | 6.33 | 6.25 |
| | 202 | 6.81 | 6.65 | 7.05 | 6.33 | 5.37 |
| | 203 | 6.41 | 7.30 | 7.21 | 6.73 | 6.17 |
| | 204 | 6.57 | 6.09 | 6.17 | 5.93 | 5.85 |
| | Mean | 6.37 | 6.59 | 6.77 | 6.33 | 5.91 |
| | S.E. | 0.24 | 0.26 | 0.23 | 0.16 | 0.20 |
| control | 101 | 5.37 | 6.33 | 6.97 | N.D. | 6.73 |
| | 102 | 6.01 | 7.21 | 7.46 | N.D. | 8.34 |
| | 103 | 6.01 | 7.54 | 7.38 | N.D. | 7.70 |
| | 104 | 4.97 | 6.17 | 7.30 | N.D. | 8.02 |
| | Mean | 5.59 | 6.81 | 7.28 | N.D. | 7.70 |
| | S.E. | 0.26 | 0.33 | 0.11 | N.D. | 0.35 |

TABLE 25

Trend of Left Ventricular Anterior Wall End-Diastolic Thickness (LVAWd = IVSTd) of the Rat Heart Failure Model due to the difference in dosage of the CD106+ Human Fibroblasts (represented as "VCF" in the table)

| Groups | Animal Number | IVSTd (mm) at each week after cell injection | | | | |
|---|---|---|---|---|---|---|
| | | 0 W | 2 W | 4 W | 6 W | 8 W |
| +VCF (2.0e6 cells/50 µL) | 110 | 1.36 | 1.52 | 1.92 | 1.44 | 1.76 |
| | 111 | 1.76 | 1.20 | 1.92 | 1.44 | 1.52 |
| | 112 | 1.36 | 1.04 | 0.80 | 1.04 | 1.20 |
| | 113 | 1.20 | 1.52 | 1.28 | 1.20 | 1.36 |
| | Mean | 1.42 | 1.32 | 1.48 | 1.28 | 1.46 |
| | S.E. | 0.12 | 0.12 | 0.27 | 0.10 | 0.12 |
| +VCF (5.0e5 cells/50 µL) | 201 | 1.44 | 1.36 | 1.12 | 1.20 | 1.20 |
| | 202 | 1.04 | 1.20 | 1.12 | 1.12 | 2.08 |
| | 203 | 1.28 | 1.12 | 1.28 | 0.88 | 1.36 |
| | 204 | 1.20 | 2.00 | 1.36 | 2.24 | 1.60 |
| | Mean | 1.24 | 1.42 | 1.22 | 1.36 | 1.56 |
| | S.E. | 0.08 | 0.20 | 0.06 | 0.30 | 0.19 |

TABLE 25-continued

Trend of Left Ventricular Anterior Wall End-Diastolic Thickness (LVAWd = IVSTd) of the Rat Heart Failure Model due to the difference in dosage of the CD106+ Human Fibroblasts (represented as "VCF" in the table)

| Groups | Animal Number | IVSTd (mm) at each week after cell injection | | | | |
|---|---|---|---|---|---|---|
| | | 0 W | 2 W | 4 W | 6 W | 8 W |
| control | 101 | 2.65 | 1.20 | 1.44 | N.D. | 1.20 |
| | 102 | 2.40 | 1.20 | 1.04 | N.D. | 0.72 |
| | 103 | 1.84 | 0.72 | 0.96 | N.D. | 0.80 |
| | 104 | 2.16 | 1.12 | 1.36 | N.D. | 0.96 |
| | Mean | 2.26 | 1.06 | 1.20 | N.D. | 0.92 |
| | S.E. | 0.17 | 0.11 | 0.12 | N.D. | 0.11 |

TABLE 26

Trend of Left Ventricular Posterior Wall End-Diastolic Thickness (LVPWTd) of the Rat Heart Failure Model due to the difference in dosage of the CD106+ Human Fibroblasts (represented as "VCF" in the table)

| Groups | Animal Number | LVPWTd (mm) at each week after cell injection | | | | |
|---|---|---|---|---|---|---|
| | | 0 W | 2 W | 4 W | 6 W | 8 W |
| +VCF | 110 | 1.36 | 1.20 | 2.08 | 2.08 | 1.68 |
| (2.0e6 cells/50 μL) | 111 | 1.20 | 1.68 | 1.76 | 1.84 | 1.84 |
| | 112 | 1.36 | 1.44 | 1.68 | 1.68 | 1.68 |
| | 113 | 2.00 | 1.84 | 1.76 | 1.76 | 2.08 |
| | Mean | 1.48 | 1.54 | 1.82 | 1.84 | 1.82 |
| | S.E. | 0.18 | 0.14 | 0.09 | 0.09 | 0.09 |
| +VCF | 201 | 1.60 | 1.60 | 1.20 | 1.84 | 1.76 |
| (5.0e5 cells/50 μL) | 202 | 1.76 | 1.12 | 1.68 | 1.44 | 1.20 |
| | 203 | 1.20 | 1.28 | 1.76 | 1.28 | 1.68 |
| | 204 | 1.28 | 1.20 | 1.28 | 1.84 | 1.60 |
| | Mean | 1.46 | 1.30 | 1.48 | 1.60 | 1.56 |
| | S.E. | 0.13 | 0.11 | 0.14 | 0.14 | 0.12 |
| control | 101 | 1.28 | 1.36 | 1.20 | N.D. | 2.08 |
| | 102 | 1.52 | 1.20 | 1.68 | N.D. | 1.84 |
| | 103 | 1.28 | 1.36 | 1.44 | N.D. | 1.68 |
| | 104 | 2.32 | 2.00 | 1.84 | N.D. | 1.76 |
| | Mean | 1.60 | 1.48 | 1.54 | N.D. | 1.84 |
| | S.E. | 0.25 | 0.18 | 0.14 | N.D. | 0.09 |

TABLE 27

Trend of Heart Rate (HR) of the Rat Heart Failure Model due to the difference in dosage of the CD106+ Human Fibroblasts (represented as "VCF" in the table)

| Groups | Animal Number | HR (bpm) at each week after cell injection | | | | |
|---|---|---|---|---|---|---|
| | | 0 W | 2 W | 4 W | 6 W | 8 W |
| +VCF | 110 | 335.00 | 359.00 | 368.00 | 313.00 | 306.00 |
| (2.0e6 cells/ | 111 | 359.00 | 343.00 | 319.00 | 313.00 | 319.00 |
| 50 μL) | 112 | 359.00 | 300.00 | 359.00 | 359.00 | 343.00 |
| | 113 | 343.00 | 335.00 | 368.00 | 319.00 | 380.00 |
| | Mean | 349.00 | 334.25 | 353.50 | 326.00 | 337.00 |
| | S.E. | 6.00 | 12.46 | 11.69 | 11.09 | 16.25 |
| +VCF | 201 | 380.00 | 351.00 | 351.00 | 359.00 | 351.00 |
| (5.0e5 cells/ | 202 | 390.00 | 411.00 | 328.00 | 359.00 | 390.00 |
| 50 μL) | 203 | 359.00 | 343.00 | 343.00 | 343.00 | 343.00 |
| | 204 | 351.00 | 313.00 | 335.00 | 351.00 | 313.00 |
| | Mean | 370.00 | 354.50 | 339.25 | 353.00 | 349.25 |
| | S.E. | 9.05 | 20.53 | 4.97 | 3.83 | 15.86 |
| control | 101 | 380.00 | 368.00 | 343.00 | N.D. | 319.00 |
| | 102 | 435.00 | 368.00 | 359.00 | N.D. | 359.00 |
| | 103 | 306.00 | 343.00 | 328.00 | N.D. | 328.00 |
| | 104 | 400.00 | 335.00 | 380.00 | N.D. | 343.00 |
| | Mean | 380.25 | 353.50 | 352.50 | N.D. | 337.25 |
| | S.E. | 27.23 | 8.53 | 11.14 | N.D. | 8.78 |

<Therapeutic Effect of CD106+ Human Fibroblasts on Pig Chronic Heart Failure Model>

Figure 15:
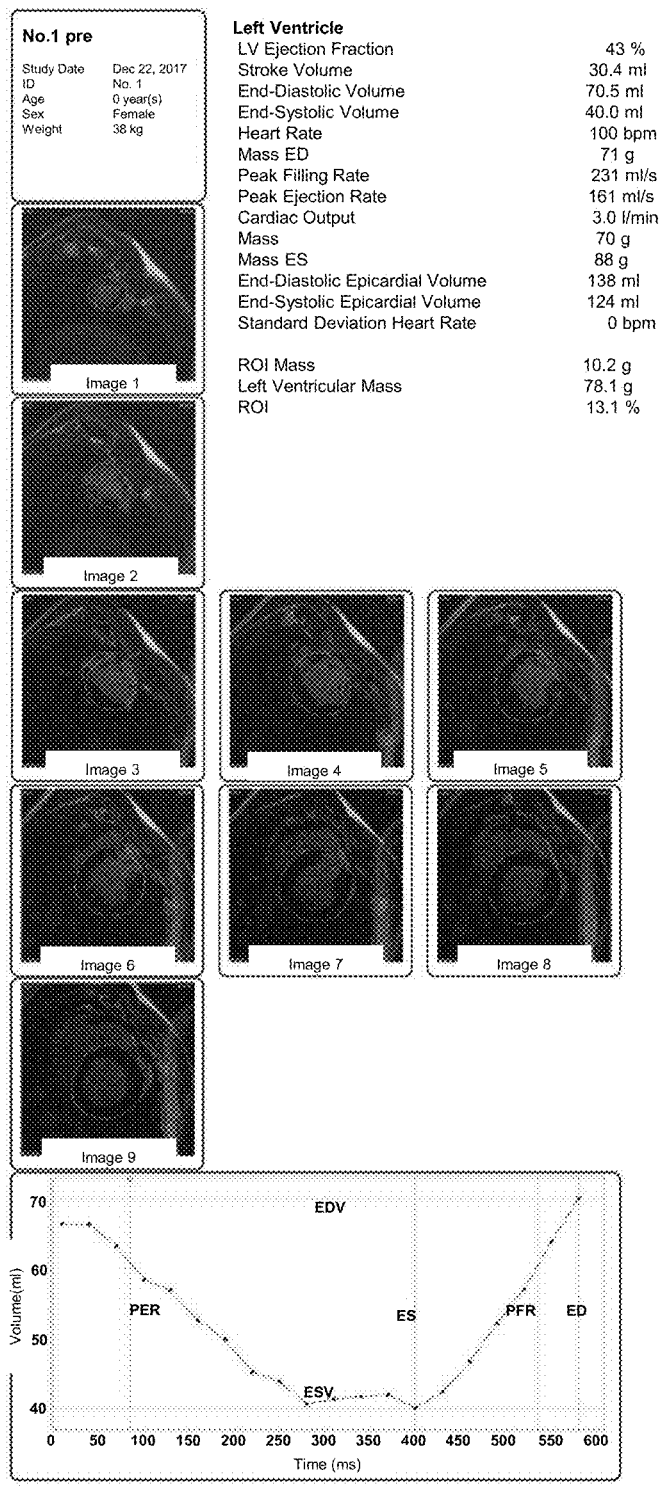
FIG. 15 shows the results of evaluation of heart functions in a pig chronic heart failure model, which evaluation was carried out on the day before administration of CD106-positive human fibroblasts (drawing-substituting photographs).
Figure 16:
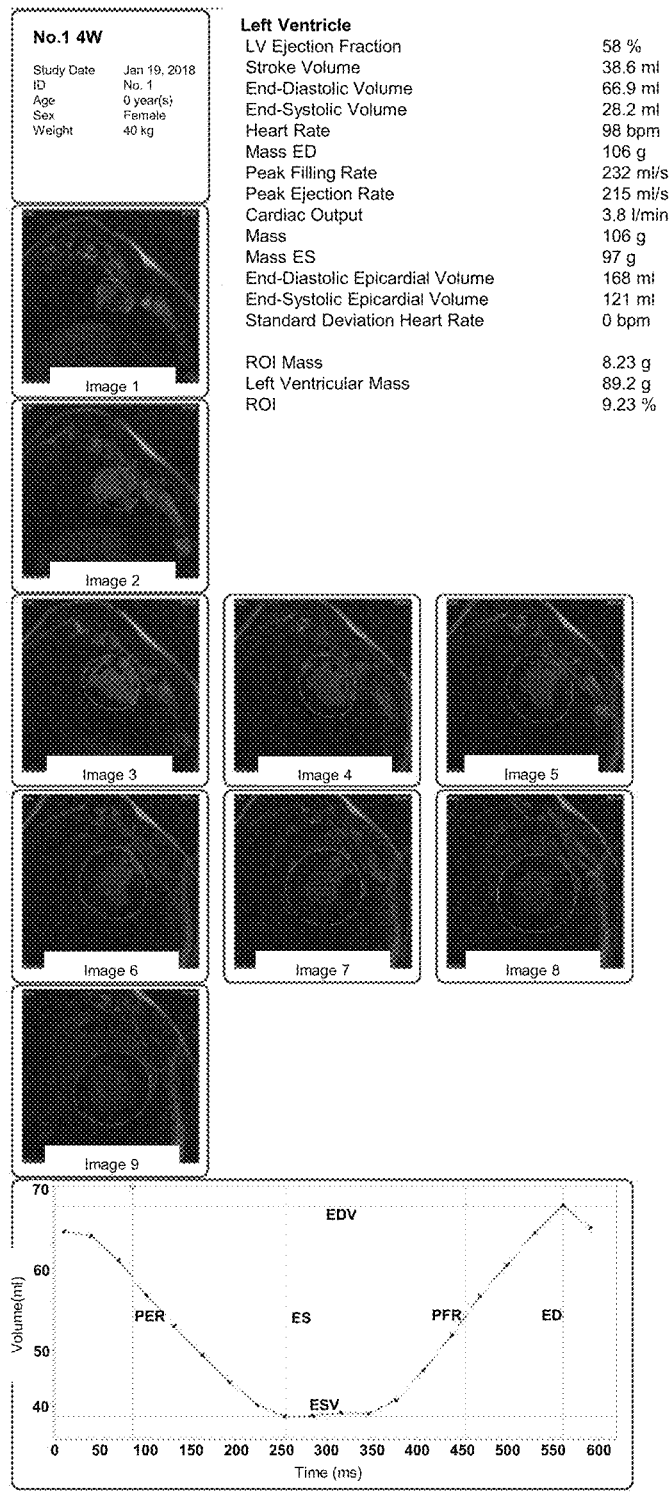
FIG. 16 shows the results of evaluation of heart functions in a pig chronic heart failure model, which evaluation was carried out four weeks after administration of CD106-positive human fibroblasts (drawing-substituting photographs).
Figure 17:
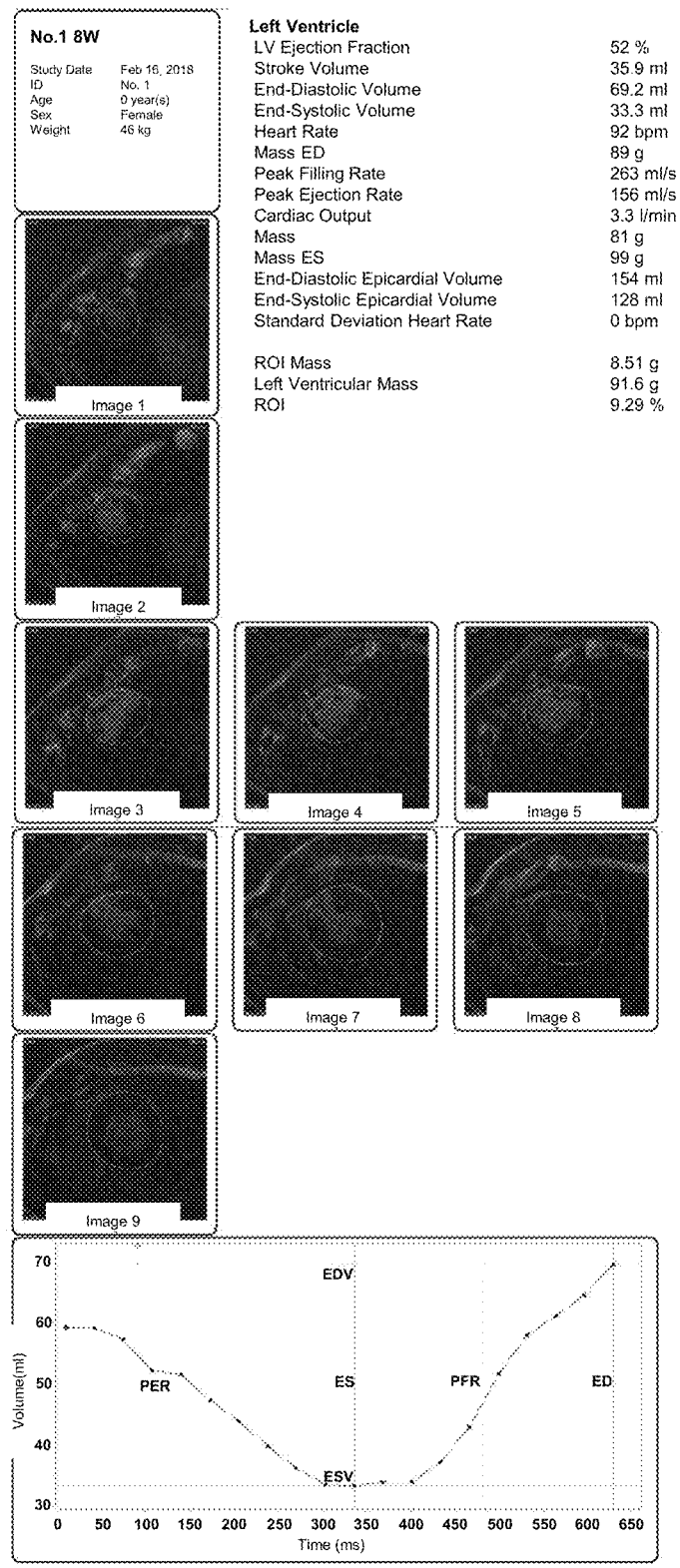
FIG. 17 shows the results of evaluation of heart functions in a pig chronic heart failure model, which evaluation was carried out eight weeks after administration of CD106-positive human fibroblasts (drawing-substituting photographs).

Subsequently, a chronic heart failure model was prepared using pig, whose heart is reported to be anatomically and physiologically close to the heart of human, and the therapeutic effect of CD106+ human fibroblasts on the heart failure was evaluated. The results are shown in FIGS. 15, 16, and 17. On the day before the administration of the CD106+ human fibroblasts, LVEF was 43%; SV was 30.4 mL; EDV was 70.5 mL; ESV was 40.0 mL; HR was 100 bpm; PFR was 231 mL/s; and PER was 161 mL/s. Since the infarct weight (fibrotic area weight) as calculated by ROI analysis was 10.2 g, and the left ventricular cardiac muscle weight was 78.1 g, the infarct region (fibrotic area) (%) was found to be 13.1%.

On the other hand, at Week 4 after the administration of the CD106+ human fibroblasts, LVEF was 58%; SV was 38.6 mL; EDV was 66.9 mL; ESV was 28.2 mL; HR was 98 bpm; PFR was 232 mL/s; and PER was 215 mL/s. It became clear that improvement of LVEF by 15% and improvement of SV by 8.2 mL can be achieved at Week 4 after the administration of the CD106+ human fibroblasts. Further, since ESV decreased by 11.8 mL, and PER increased by 54 mL/s, improvement of the cardiac functions became clear. Further, since the infarct weight (fibrotic area weight) as calculated by ROI analysis was 8.23 g, and the left ventricular cardiac muscle weight was 89.2 g, the infarct region (fibrotic area) (%) was found to be 9.23%. From this result, it became clear that administration of the CD106+ human fibroblasts cause reduction of the infarct weight (fibrotic area weight) by 1.97 g.

At Week 8 after the administration of the CD106+ human fibroblasts, LVEF was 52%; SV was 35.9 mL; EDV was 69.2 mL; ESV was 33.3 mL; HR was 92 bpm; PFR was 263 mL/s; and PER was 156 mL/s. It became clear that improvement of LVEF by 8% can be achieved at Week 8 after the administration of the CD106+ human fibroblasts. Further, since the infarct weight (fibrotic area weight) as calculated by ROI analysis was 8.51 g, and the left ventricular cardiac muscle weight was 91.6 g, the infarct region (fibrotic area) (%) was found to be 9.29%. From this result, it became clear that administration of the CD106+ human fibroblasts cause reduction of the infarct weight (fibrotic area weight) by 1.69 g in eight weeks after the administration. The infarct/fibrotic area (%) hardly changed from that at Week 4 after the transplantation. From this result, it became clear that CD106+ human fibroblasts are highly effective for recovery of cardiac functions also in heart failure of pig, which is reported to be anatomically and physiologically close to human.

Figure 18:
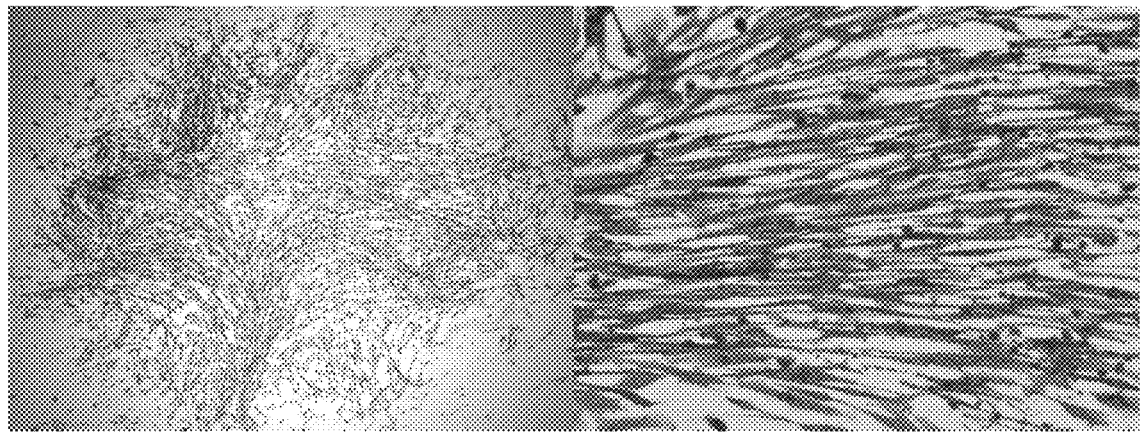
FIG. 18 shows a microscope image of the CD106+ Human Fibroblasts (VCF).
Figure 18:
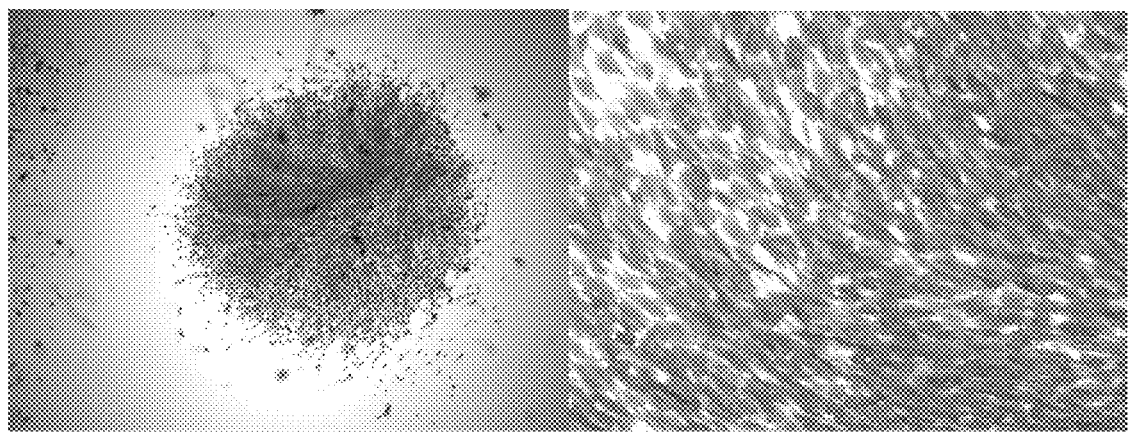

A microscope image of the CD106+ Human Fibroblasts (VCFs) is shown in FIG. 18. The VCFs did not form colonies, and this image suggests that the VCFs are readily distinguishable from mesenchymal stem cells (MSCs).

The invention claimed is:

1. A method for treatment of a heart disease, the method comprising:
   providing a composition comprising fibroblasts, the fibroblasts comprising CD106-positive fibroblasts wherein the ratio in terms of the cell number of the CD106-positive fibroblasts to the total amount of cells contained in the composition is not less than 70%; and
   carrying out injection of the composition into a necrotic cardiac tissue region or a vicinity thereof, and/or infusion of the composition into a coronary artery, wherein the heart disease is selected from the group consisting of heart failure, ischemic heart disease, and myocardial infarction.

2. The method for treatment of a heart disease according to claim 1, wherein the fibroblasts comprise CD90-positive fibroblasts.

3. The method for treatment of a heart disease according to claim 1, wherein the fibroblasts comprise connexin 43-positive fibroblasts.

4. The method for treatment of a heart disease according to claim 1, wherein the ratio in terms of the cell number of cardiomyocytes to the total cells contained in the injectable composition is not more than 5%.

5. The method for treatment of a heart disease according to claim 1, wherein the ratio in terms of the cell number of the CD106-positive fibroblasts to the total amount of cells contained in the composition is not less than 80%.

* * * * *